(12) United States Patent
Delage et al.

(10) Patent No.: US 10,179,921 B2
(45) Date of Patent: Jan. 15, 2019

(54) METHOD FOR PRODUCING POLYPHENOL COMPOUNDS

(71) Applicants:CENTRE NATIONAL DE LA RECHERCHE SCIENTIFIQUE (C.N.R.S), Paris (FR); UNIVERSITÉ PIERRE ET MARIE CURIE (PARIS 6), Paris (FR)

(72) Inventors: Ludovic Delage, Mespaul (FR); Laurence Meslet-Cladiere, Saint-Pol-de-Leon (FR); Philippe Potin, Roscoff (FR); Sophie Goulitquer, Brest (FR)

(73) Assignees: UNIVERSITÉ PIERRE ET MARIE CURIE (PARIS 6), Paris (FR); CENTRE NATIONAL DE LA RECHERCHE SCIENTIFIQUE (C.N.R.S), Paris (FR)

( * ) Notice: Subject to any disclaimer, the term of this patent is extended or adjusted under 35 U.S.C. 154(b) by 0 days.

(21) Appl. No.: 14/348,490

(22) PCT Filed: Sep. 26, 2012

(86) PCT No.: PCT/EP2012/068994
§ 371 (c)(1),
(2) Date: Jul. 1, 2014

(87) PCT Pub. No.: WO2013/045510
PCT Pub. Date: Apr. 4, 2013

(65) Prior Publication Data
US 2014/0315269 A1    Oct. 23, 2014

(30) Foreign Application Priority Data

Sep. 29, 2011  (FR) ..................................... 11 58728

(51) Int. Cl.
| C12N 1/22 | (2006.01) |
| C12P 7/22 | (2006.01) |
| C12N 9/10 | (2006.01) |
| C12N 15/52 | (2006.01) |
| C12N 9/00 | (2006.01) |

(52) U.S. Cl.
CPC .............. *C12P 7/22* (2013.01); *C12N 9/1029* (2013.01); *C12N 9/93* (2013.01); *C12N 15/52* (2013.01); *C12Y 203/01094* (2013.01)

(58) Field of Classification Search
None
See application file for complete search history.

(56) References Cited

U.S. PATENT DOCUMENTS

| 5,354,844 A | 10/1994 | Beug et al. |
| 5,792,645 A | 8/1998 | Beug et al. |
| 7,943,362 B2 | 5/2011 | Frost |
| 8,329,445 B2 | 12/2012 | Frost |
| 2007/0178571 A1 | 8/2007 | Frost |
| 2011/0183391 A1 | 7/2011 | Frost |

FOREIGN PATENT DOCUMENTS

| CA | 2012311 | 9/1990 |
| WO | WO2006/044290 | 4/2006 |

OTHER PUBLICATIONS

Zha et al. (JBC, vol. 281, No. 42, pp. 32036-32047, 2006).*
Baharum et al. (Marine Biotechnol., vol. 13 (5), pp. 845-856, 2011.*
J. Mark Cock et al: "The Ectocarpus genome and the independent evolution of multicellularity in brown algae", Nature, vol. 465, No. 7298, Jun. 3, 2010 (Jun. 3, 2010), pp. 617-621.
Inder Pal Singh et al: "Phloroglucinol compounds of therapeutic interest: global patent and technology status", Expert Opinion on Therapeutic Patents, vol. 19, No. 6, Jun. 1, 2009 (Jun. 1, 2009), pp. 847-866.
Hariyanti Baharum et al: Molecular Cloning, Modeling, and Site-Directed Mutagenesis of Type III Polyketide Synthase from(Phaeophyta)rl, Marine Biotechnology, Springer-Verlag, NE, vol. 13, No. 5, Dec. 23, 2010 (Dec. 23, 2010), pp. 845-856.
Sophie _Goulitquer, "METABOMER: La plate-forme de metabolomique de la Station Biologique de Roscoff." Extrait de l'Internet: URL:http://genowebl.irisa.fr/OGP/ftp/Presentations/Presentation_ Sophie _GOULITQUER.pdf Nov. 22, 2010 (Nov. 22, 2010).
International Search Report, dated Nov. 27, 2012, which issued during the prosecution of European Patent Application No. PCT/EP2012/068994, which corresponds to the present application.
Abe et al., "A Plant Type III Polyketide Synthase that Prodcues Pentaketide Chromone" J. Am. Chem. Soc. 2005, 127(5):1362-1363.
Austin et al., "Biosynthesis of Dictyostelium discoideum differentiation-inducing factor by a hybrid type I fatty acid-type III polyketide synthase" Nature Chemical Biology 2006, 2(9):494-502.
Baharum et al., "Molecular Cloning, Modeling, and Site-Directed Mutagenesis of Type III Polyketide Synthase from Sargassum binderi (Phaeophyta)" Mar Biotechnol 2011, 13(5):845-856.
Izumikawa et al., "Expression and characterization of the type III polyketide synthase 1,3,6,8-tetrahydroxynaphthalene synthase from Streptomyces coelicolor A3(2)" Ind Microbiol Biotechnol 2003, 30:510-515.
Mizuuchi et al., "Structure Function Analysis of Novel Type III Polyketide Synthases from *Arabidopsis thaliana*" Biol. Pharm. Bull. 2008, 31(12):2205-2210.

(Continued)

*Primary Examiner* — Hope Robinson
(74) *Attorney, Agent, or Firm* — Troutman Sanders LLP

(57) ABSTRACT

The present invention relates to a method for producing polyphenol compounds, i.e. phloroglucinol or one of its derivatives, with a polyketide synthase of type III (PKSIII) from a brown marine alga. The invention also relates to recombinant nucleic acids coding for a polyketide synthase of type III (PKSIII) from the brown alga *Ectocarpus siliculosus* (*E. siliculosus*), to recombinant vectors comprising these nucleic acids, as well as to host cells comprising these vectors. Finally, the invention relates to a method for preparing of various compounds by means of polyphenol compounds produced according to the aforementioned method.

3 Claims, 7 Drawing Sheets
Specification includes a Sequence Listing.

(56) References Cited

OTHER PUBLICATIONS

Nielsen et al., "Machine learning approaches for the predication of signal peptides and other protein sorting signals" Protein Engineering 1999, 12(1):3-9.

Sankaranarayanan et al., "A novel tunnel in mycobacterial type III polyketide synthase reveals the structural basis for generating diverse metabolites" Nature Structural & Molecular Biology 2004, 11(9):894-900.

Singh et al., "Phloroglucinol compounds of therapeutic interest: global patent and technology status" Expert Opin. Ther. Patents 2009, 19:847-66.

Wanibuchi et al., "Enzymatic formation of an aromatic dodecaketide by engineered plant polyketide synthase" Bioorganic & Medicinal Chemistry Letters 2011, 21:2083-2086.

Waterman et al.,"Analysis of phenolic plant metabolites" Blackwell Scientific Publications: Oxford, Great Britain 1994.

Wu et al., "Receptor-mediated Gene Delivery and Expression in Vivo*" The Journal of Biological Chemistry 1988, 263(29):14621-14624.

Wilson et al., "Hepatocyte-directed Gene Transfer in Vivo Leads to Transient Improvement of Hypercholesterolemia in Low Density Lipoprotein Receptor-deficient Rabbits*" The Journal of Biological Chemistry 1988 1992, 267(2):963-967.

Nobutaka Funa, et al., "Pentaketide Resorcylic Acid Synthesis by Type III Polyketide Synthase from Neurospora crassa*", The Journal of Biological Chemistry vol. 282, No. 19, pp. 14476-14481, May 11, 2007.

Yanyan Li, Rolf Müller, "Review: Non-modular polyketide synthases in myxobacteria", Phytochemistry 70 (2009), pp. 1850-1857.

Bradley S. Moore, et al., "Review: Plant-like Biosynthetic Pathways in Bacteria: From Benzoic Acid to Chalcone", J. Nat. Prod. 2002, 65, pp. 1956-1962.

Philippe Potin, et al., "Algal Genomics May Offer New Insights into Searweed", UPMC Paris University, 2010.

Laurence Meslet-Cladière,, et al., "Structure/Function Analysis of a Type III Polyketide Synthase, in the Brown Alga *Ectocarpus siliculosus* Reveals a Biochemical Pathway in Phlorotannin Monomer Biosynthesis", The Plant Cell, vol. 25: 3089-3103, Aug. 2013.

\* cited by examiner

Coverage of the PKS1 sequence:

SKDEQTYYPVIAGMAIGNPQYRCTQNEALAVASKCPGIESIKPVLER
IYGNSRIGSRYPAVPDFTPGRAAKGDPLFYPADGSYQVPVDVRLDKF
KEKAVPLVSDVAPRATKEAGLNVEDISKLVVVSSTGFLGPGLDCELI
KNLGLTRSVDRTLIGFMSCAAAMNGFRNANDTVTANPGKYALMICVE
LSSVHTTFDDMINDAILHAIFADGCAAAVTLKCQARKSECPKGTLAIVD
NHAWLMEGTEDGITLAIKPNGITCTLSKFLPQYIAKNIAFFADGFLK
KHKLGRDDVDPWCVHPGGRRIIEEAQNGLGLSEEQTADSWAVLGEYG
NMLSPSVMPVLSRVFKRHNAALAQGKPGYQTGMAFSFSEGVGAEGIL
LRQI (SEQ ID NO:3)

Identification:
Mass: 44433, Score: 163, Expectation: 6e-10, Matches: 32
gi|299471698 Polyketide Synthase III [Ectocarpus siliculosus]

FIG.2

List of peaks (peptide mass m/z)
709.3434
804.2637
808.2713
832.2990
918.4548
1026.5706
1182.6604
1269.5841
1273.6055
1480.7358
1497.7590
1559.6200
1886.8108
1891.7970
2095.9417
2223.0097
2366.0989
2356.0971
2771.3205
2785.3423
3246.5380

METHOD FOR PRODUCING POLYPHENOL COMPOUNDS

CROSS-REFERENCE TO RELATED APPLICATIONS

This application is the U.S. National Stage under 37 U.S.C. § 371 of International Application No. PCT/EP2012/068994, filed Sep. 26, 2012, which claims priority to French Application No. 1158728, filed Sep. 29, 2011. The International Application published on Apr. 4, 2013 as WO 2013/045510. All of the above applications are incorporated by reference in their entireties.

SEQUENCE LISTING

The instant application contains a Sequence Listing which has been submitted in ASCII format via EFS-Web and is hereby incorporated by reference in its entirety. Said ASCII copy, created on Mar. 28, 2014, is named upmc-seq-listing_ST25, and is 11,288 bytes in size.

FIELD OF THE INVENTION

The present invention relates to a method for producing polyphenol compounds, i.e. phloroglucinol or one of its derivatives, with a polyketide synthase of type III (PKSIII) from a brown marine alga. The invention also relates to recombinant nucleic acids coding for a polyketide synthase of type III (PKSIII) of the brown alga *Ectocarpus siliculosus* (*E. siliculosus*), to recombinant vectors comprising these nucleic acids, as well as to host cells comprising these vectors. Finally, the invention relates to a method for preparing various compounds by means of polyphenol compounds produced according to the aforementioned method.

BACKGROUND

Secondary polyphenol metabolites form a wide group of diverse chemical compounds which exist both in land plants and in aquatic macrophytes (Waterman and Mole, 1994, Analysis of phenolic plant metabolites, *Blackwell Scientific Publications: Oxford, Great Britain*). From among these compounds, phloroglucinol as well as its derivatives are widely used in industry, and notably in the pharmaceutical, cosmetic or further agri-feed industries. More recently, phloroglucinol and its derivatives have shown potentially interesting activities for humans in pharmacology (production of reaction intermediates for hemi-synthesis of chemical compounds), in medicine (antimicrobial, anti-HIV, anti-cancer, anti-diabetic, anti-allergic, anti-inflammatory properties) or cosmetics (anti-age effect) which makes them natural molecules with a very interesting potential (Singh I P et al., 2009, *Expert Opin Ther Pat*, 19: 847-66, for a review). At the present time, only phloroglucinol synthesized chemically is marketed as a musculotropic antispasmodic drug (under the name of Spasfon® in France). Moreover, mixtures of products are also marketed like extracts of *Ascophyllum nodosum* by the Algues & Mer Ouessant corporation (29, France), products like Seanol™, extracts of *Ecklonia cava* or further HealSea, extracts of *Fucus vesiculosus* by the Diana Naturals corporation (35, France) and a few other companies worldwide.

SUMMARY

One of the present major challenges is therefore to provide methods for producing phloroglucinol or its derivatives, which are effective and rapid, and which give the possibility of obtaining these compounds in large proportions. One of the possibilities consists of producing it via a biosynthesis route applying the use of enzymes.

Among these enzymes potentially capable of synthesizing phloroglucinol, polyketide synthases of type III (PKS III) which are key enzymes of the secondary metabolism in land plants (flavonoid root, biosynthesis of phytoalexins) but also in bacteria, fungi and a few protozoa are notably distinguished. The corresponding PKS III (chalcone synthases, stilbene synthases, pyrone synthases . . . ) share the same reaction mechanism but differ by their substrate specificity for <<starter>> molecules and by the stereochemistry of the cyclization reaction giving rise to a wide panel of secondary polyphenol metabolites having very diverse functions.

Many polyketide synthases were thus isolated from various organisms, such as the brown algae *Sargassum binderi*, the land plants *Aloe arborescens* and *Arabidopsis thaliana*, the amoebae *Dictyostelium discoideum*, or further the bacteria *Mycobacterium tuberculosis*, *Streptomyces coelicolor* and *Pseudomonas fluorescens* (Baharum et al., *Mar Biotechnol*, 2011, 13(5): 845-856; Wanibuchi et al., *Bioorg Med Chem Lett*, 2011, 21: 2083-2086; Abe et al., *J Am Chem Soc*, 2005, 127(5): 1362-1363; Mizuuchi et al., *Biol Pharm Bull*, 2008, 31(12): 2205-2210; Austin et al., *Nat Chem Biol*, 2006, 2(9): 494-502; Sankaranarayanan et al., *Nat Struct Mol Biol*, 2004, 11(9): 894-900; Izumikawa et al., *J Ind Microbiol Biotechnol*, 2003, 30: 510-515; WO2006/044290). Among these polyketide synthases, only the polyketide synthase PhID stemming from the bacterium *Pseudomonas fluorescens* is capable of synthesizing phloroglucinol by using malonyl-CoA as a <<starter>> molecule (WO2006/044290). The other polyketide synthases, although also using malonyl-CoA as a <<starter>> molecule, are unfortunately incapable of synthesizing phloroglucinol.

The inventors have identified a novel polyketide synthase in the brown marine alga *Ectocarpus siliculosus*, which was called PKS1. For the first time, the inventors have produced a polyketide synthase of type III (PKS III) of a brown marine alga in a recombinant way and active in a heterologous system (the bacterium *Escherichia coli*) with an established homogeneity purification procedure allowing production of about 5 to 10 mg of pure protein per liter of culture. The inventors have also shown that this PKS1 was capable of synthesizing in vitro phloroglucinol from the malonyl-coenzyme A (malonylCoA). Further, other products obtained from malonylCoA and from several acylCoA with more or less long aliphatic chains (hexanoylCoA, decanoylCoA, lauroylCoA and palmitoylCoA) are present in the reactions.

Nucleic Acid, Protein and Method for Producing the Enzyme

The present invention relates to an isolated nucleic acid comprising or consisting in the sequence SEQ ID NO: 2 or SEQ ID NO: 4, or in a sequence at least 85% identical with the sequence SEQ ID NO: 2 or SEQ ID NO: 4, or in a complementary sequence of SEQ ID NO: 2 or of SEQ ID NO: 4.

Preferably, said isolated nucleic acid codes for a polyketide synthase of type III.

The present invention additionally relates to an isolated nucleic acid coding for a polyketide synthase of type III (PKS III) comprising or consisting in:
  a) The nucleotide sequence SEQ ID NO: 2,
  b) The nucleotide sequence SEQ ID NO: 4,
  c) The complementary sequence of SEQ ID NO: 2 or of SEQ ID NO: 4, d) A sequence at least 85% identical with SEQ ID NO: 2 or with SEQ ID NO: 4, e) A sequence differing from the sequences a) to d) by degeneration of the code, f) A nucleotide sequence hybridizing under specific stringency conditions with at least one of the sequences a) to e).

The invention will be further illustrated by the following figures and examples.

DESCRIPTION OF THE FIGURES

FIG. 2. represents the mass spectrometry analysis of the purified recombinant protein PKS1 of E. siliculosus.

DETAILED DESCRIPTION

Figure 1:
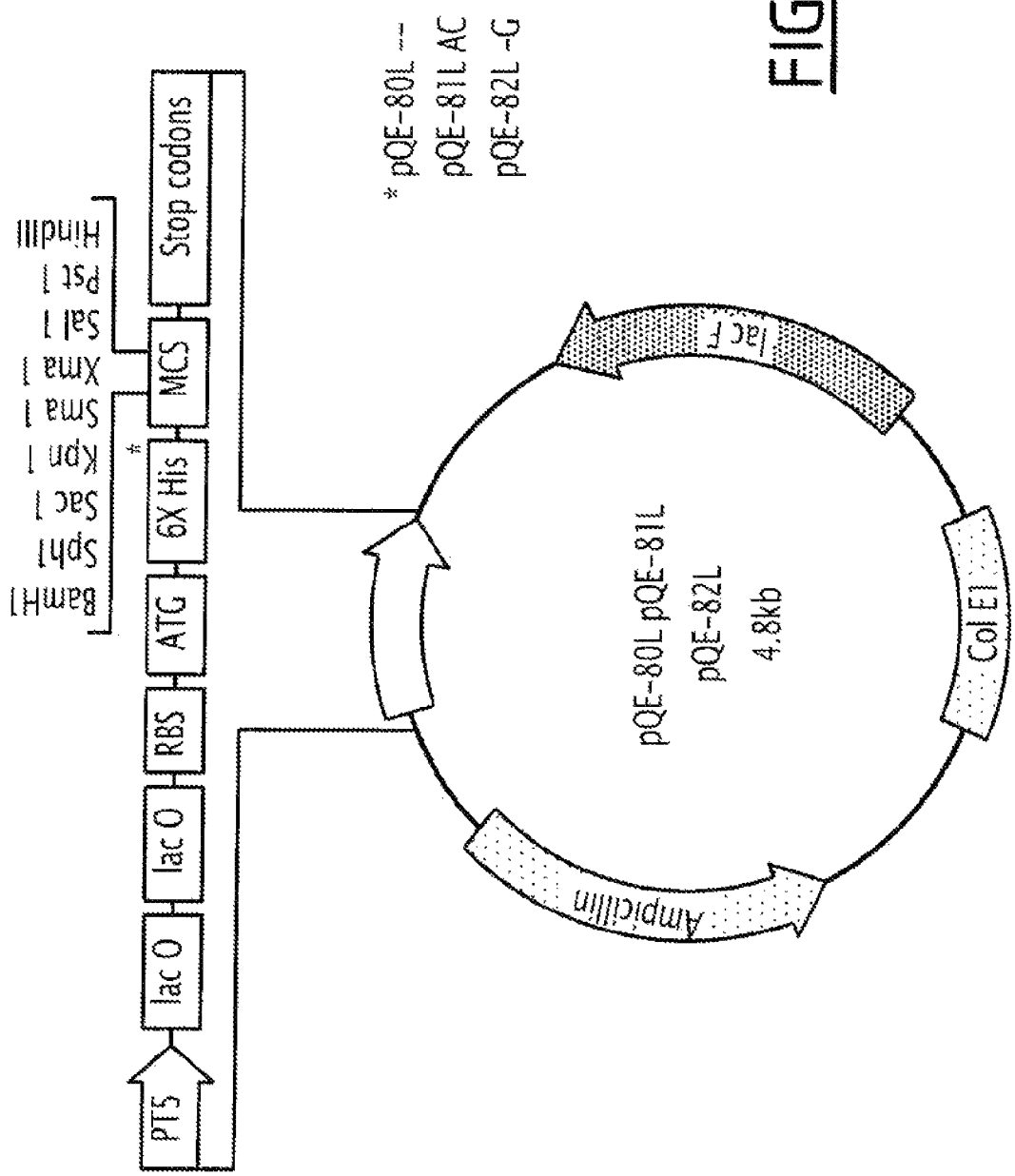
FIG. 1. represents the expression vector pQE-80L (Qiagen) containing the promoter of the bacteriophage T5 inducible by isopropyl-b-D-thiogalactopyranoside (IPTG) used for the expression of the PKS1 protein.

By <<isolated>>, is meant a compound which has been isolated from a living organism, such as an alga, or an animal, and/or a library of compounds. Preferably, the isolated nucleic acid stems from a brown marine alga. Still more preferably, the isolated nucleic acid stems from the brown marine alga Ectocarpus siliculosus (E. siliculosus).

Preferentially, the nucleic acids according to the invention are recombinant nucleic acids. By <<recombinant nucleic acid>>, is meant a nucleic acid, i.e. a DNA or RNA molecule, which has been subject to a biological molecular manipulation.

By <<nucleic acid>>, is meant the phosphate ester polymeric form of ribonucleosides (adenosine, guanosine, uridine or cytidine; "RNA molecules") or deoxyribonucleosides (deoxyadenosine, deoxyguanosine, deoxythymidine or deoxycytidine; "DNA molecules") in a monocatenary form or in the form of a bicatenary helix. DNA-DNA, DNA-RNA and RNA-RNA bicatenary helices are possible. The term of nucleic acid, and in particular of DNA or RNA molecule only refers to the primary or secondary structure of the molecule, and is by no means limited to particular tertiary forms. Thus, this term comprises bicatenary DNA which inter alia is found in linear or circular DNA molecules (for example restriction fragments), viruses, plasmids and chromosomes. When the structure of particular bicatenary DNA molecules is mentioned, the sequences may be described here according to the normal convention which only gives a sequence in the direction of 5' to 3' along the non-transcribed strand of the DNA (i.e. the strand having a homologous sequence to mRNA).

By a sequence at least 85% identical with a reference sequence, is meant that the sequence is identical to the reference sequence, except that the sequence may include up to 15 alterations of nucleotides every 100 nucleotides of the reference sequence. In other words, in order to obtain a sequence at least 85% identical with the reference sequence, up to 15% of the nucleotides of the sequence may be inserted, deleted or substituted with another nucleotide.

The identity percentage may be computed by producing an overall pair wise alignment based on the Needleman-Wunsch alignment algorithm for finding the optimum alignment (including "holes" or "gaps") between two sequences over the whole of their length, for example by using Needle, and by using the BLOSUM62 matrix with a penalty for inserting <<gaps>> of 10 and a penalty of extension of <<gaps>> of 0.5.

Preferably, the nucleotide sequence of the invention, notably the sequence c) is at least 90%, 91%, 92%, 93%, 94%, 95%, or 99% identical with the sequence SEQ ID NO: 2 or SEQ ID NO: 4.

By <<sequence differing from the sequences a) to c) by degeneration of the code>>, is meant a sequence which differs from the reference sequence by a conservative substitution as indicated in the table below.

| Conservative substitutions | Type of amino acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with non-charged polar side chains |
| Asp, Glu | Amino acids with acid side chains |
| Lys, Arg, His | Amino acids with basic side chains |
| Gly | Neutral side chain |

A nucleic acid molecule "may hybridize" to another nucleic acid molecule such as a DNA, a genomic DNA or an RNA, when the monocatenary shape of the nucleic acid molecule may hybridize with the other nucleic acid molecule under suitable conditions of temperature and of ionic force of the solution (see Sambrook et al., supra). The temperature and ionic force conditions determine the "stringency" of the hybridization. Low stringency hybridization conditions correspond to a $T_m$ of 55° C., for example SSC 5×, SDS 0.1%, milk 0.25%, and no formamide; or 30% formamide, SSC 5×, 0.5% SDS). Moderate stringency hybridization conditions correspond to a higher $T_m$ (about 60° C.), for example 40% formamide, with SSC 5× or 6×. High stringency hybridization conditions correspond to the highest $T_m$ (greater than or equal to about 65° C.), for example 50% formamide, SSC 5× or 6×. Hybridization requires that both nucleic acid molecules contain complementary sequences, although depending on the stringency of the hybridization, mismatches between the bases are possible. The suitable stringency for hybridization of the nucleic acid molecules depends on the length of the nucleic acid molecules and on the complementation degree, variables well known to those skilled in the art. The higher the degree of similarity or homology between two nucleotide sequences, the higher is the value of the $T_m$ for the hybrids of nucleic acid molecules having these sequences. The relative stability (corresponding to a higher $T_m$) of nucleic acid hybridizations decreases in the following order: RNA:RNA, DNA:RNA, DNA:DNA. For hybrids with a length of more than 100 nucleotides, equations for computing $T_m$ were derived (see Sambrook et al., supra, 9.50-0.51). For hybridization with shorter nucleic acid molecules, i.e. oligonucleotides, the position of the mismatches becomes more significant and the length of the oligonucleotide determines its specificity (see Sambrook et al., supra, 11.7-11.8). Preferably, a minimum length for a nucleic acid molecule which may hybridize is of at least about 10 nucleotides; preferably, of at least about 10 nucleotides; and more preferentially, the length is of at least about 50 nucleotides; still more preferably of at least 100 nucleotides; even more preferably of at least 1,000 nucleotides.

The term of "specific hybridization conditions" designates a $T_m$ of 55° C. and uses conditions described above. In a preferred embodiment, the $T_m$ is equal to 60° C., in an even more preferred embodiment, the $T_m$ is equal to 65° C.

A DNA "coding sequence" is a bi-catenary DNA sequence which is transcribed and translated into a polypeptide in vivo when it is placed under the control of suitable regulatory sequences. The frontiers of the coding sequence are determined by a starting codon at the end 5' (amino) and by a stopping codon for the translation at the end 3' (a carboxy). A coding sequence may include, without being limited thereto, prokaryotic sequences, DNAc stemming from eukaryotic mRNA, genomic DNA sequences from eukaryotic DNA (for example of mammals), and even synthetic DNA sequences. If the coding sequence is intended for expression in a eukaryotic cell, a polyadenylation signal and a termination sequence of the transcription will generally be located in 3' of the coding sequence.

Sequences for controlling the transcription and the translation are DNA regulatory sequences, such as promoters, activators, terminators and other similar sequences, which allow expression of a coding sequence in a host cell. In eukaryotic cells, the polyadenylation signals are control sequences.

A "promoter sequence" is a DNA regulatory region capable of binding the RNA polymerase in a cell and of initiating transcription of a coding sequence towards the downstream portion (direction 3'). In the goals defining the present invention, the promoter sequence is bound to its end 3' by the site for initiating the transcription and extends upstream (direction 5') while including the minimum number of bases or elements required for initiating transcription to detectable levels relatively to the background noise. In the promoter sequence, a site is found for initiating transcription (conveniently defined, for example by mapping with the nuclease S1), as well as domains for binding to proteins (consensus sequences) responsible for the binding of the RNA polymerase. Eukaryotic promoters will often contain but not always, "TATA" boxes and "CAT" boxes.

A coding sequence is "under the control" of sequences for controlling the transcription and the translation in a cell, when the RNA polymerase transcribes the coding sequence into mRNA which is then translated into a coded protein by the coding sequence.

A "signal sequence" may be included before the coding sequence. This sequence codes for a signal peptide, in the N-terminal position of the protein, which orders the host cell to transport the protein on the cell surface or to secrete the protein into the medium, and this signal peptide is generally selectively degraded by the cell after export. The signal sequences may be found associated with diverse native proteins of prokaryotes and eukaryotes. Preferably the signal sequence consists in or comprises the sequence 5'-ATGTCT-TCTGCTGCGGTTGCTATGCTGGCTGACCCGACT-GTCCAGATCGCTCTGGCGT GCCTGGTGGT-GTCTCTCTTCGTTGTGCTGCAGTCGGTCAAAAAG-3' (SEQ ID NO: 5). Preferably the signal sequence codes for the signal peptide of sequence MSSAAVAMLADPTVQ-IALACLWSLFWLQSVKK (SEQ ID NO: 6).

A <<tag sequence>> (or <<tag>>) may also be included before or after the coding sequence. This sequence generally codes for a repetition of histidines, in the N-terminal position of the protein, and allows purification of the protein. Preferably, the tag sequence is placed before the coding sequence, and codes for the sequence of six histidines SEQ ID NO: 7 (HHHHHH), the tag sequence may therefore have as a nucleotide sequence, the sequence SEQ ID NO: 8 (5'-CAYCAYCAYCAYCAYCAY-3'). Still more preferably, the tag sequence has for an amino acid sequence, the sequence MRGSHHHHHHGS (SEQ ID NO: 9). The nucleotide sequence corresponding to the tag sequence coding for the sequence SEQ ID NO: 9 may be the sequence 5'-ATGCGCGGCAGCCATCATCATCATCATCATG-GCAGC-3' (SEQ ID NO: 10).

In a particularly preferred embodiment, the nucleic acid according to the invention codes for a PKSIII capable of synthesizing phloroglucinol from malonyl-CoA alone or in combination with other substrates, for example acetyl-CoA, hexanoyl-CoA, decanoyl-CoA, lauroyl-CoA, or palmitoyl-CoA.

The invention also relates to a protein coded by an isolated nucleic acid according to the invention. Preferably, said protein is coded by a nucleic acid comprising or consisting in the sequence SEQ ID NO: 2 or SEQ ID NO: 4. Still more preferably, said protein comprises or consists in the sequence SEQ ID NO: 1 or SEQ ID NO: 3. Alternatively, said protein comprises or consists in a sequence having at least 93% identity, preferably at least 95% identity, or still more preferentially 99% identity with the sequence SEQ ID NO: 1 or SEQ ID NO: 3.

Preferably, said protein is a PKSIII capable of synthesizing phloroglucinol from malonyl-CoA alone or in combination with other substrates, for example acetyl-CoA, hexanoyl-CoA, decanoyl-CoA, lauroyl-CoA, or palmitoyl-CoA.

By a sequence at least 93% identical with a reference sequence, is meant that the sequence is identical with the reference sequence, except that the sequence may include up to seven alterations of amino acids per every 100 amino acids of the reference sequence. In other words, in order to obtain a sequence at least 93% identical with the reference sequence, up to 7% of the amino acids of the sequence may be inserted, deleted, or substituted with another amino acid. Preferably, the at least 93% identical sequence is a sequence homologous to the reference sequence, i.e. it differs from the reference sequence by one or several conservative substitutions.

The identity percentage may be computed by producing an overall pairwise alignment based on the Needleman-Wunsch alignment algorithm for finding the optimum alignment (including "holes" or "gaps") between two sequences over the whole of their length, for example by using Needle, and by using the BLOSUM62 matrix with a penalty for inserting <<gaps>> of 10 and a penalty for extending <<gaps>> of 0.5.

By <<conservative substitutions>>, is meant the replacement of an amino acid with another one, without altering the conformation and the function of the protein, including, but without being limited thereto, the replacement of an amino acid with another amino acid having the same properties (such as for example, the same polarities, potentials for binding to hydrogen, acid, basic, hydrophobic, aromatic and other properties). The amino acids having the same properties are known to one skilled in the art. For example, arginine, histidine and lysine are hydrophilic basic amino acids which may be interchangeable. Similarly, isoleucine, a hydrophilic amino acid, may be replaced with leucine, methionine or valine. The hydrophilic neutral amino acids which may be substituted with each other, include asparagine, glutamine, serine and threonine.

By <<substituted>> or <<modified>>, the present invention includes the amino acids which have been altered or modified from natural amino acids.

Thus, it should be understood that within the context of the invention, a conservative substitution is recognized in the state of the art as a substitution of an amino acid with another amino acid having the same properties.

Examples of conservative substitutions are given in Table 1 below:

TABLE 1

Conservative substitutions I

| Characteristics of the side chain | Amino acid |
| --- | --- |
| Non polar | G, A, P, I, L, V |
| Non-charged polar | C, S, T, M, N, Q |
| Charged polar | D, E, K, R |
| Aromatic | H, F, W, Y |
| Other | N, Q, D, E |

Alternatively, the amino acids may be grouped as described by Lehninger (1975, Biochemistry, Second Edition, Worth Publishers, Inc. New-York: NY., pp. 71-77), as described in Table 2 below:

TABLE 2

Conservative substitutions II

| Characteristics of side chain | | Amino acid |
| --- | --- | --- |
| Non-polar | Aliphatic | A, L, I, V, P |
| | Aromatic | F, W |
| | Containing sulfur | M |
| | Special case | G |
| Non-loaded polar | Hydroxyl | S,T,Y |
| | Amides | N, Q |
| | Sulfhydryl | C |
| | Special case | G |
| Positively charged (basic) | | K, R, H |
| Negatively charged (acid) | | D, E |

In another alternative, examples of conservative substitutions are given in Table 3 below:

TABLE 3

Conservative substitutions III

| Original residue | Substitution example |
| --- | --- |
| A | V L I |
| R | K Q N |
| N | Q H K R |
| D | E |
| C | S |
| G | N |
| E | D |
| H | N Q K R |
| I | L V M A F |
| L | I V M A F |
| K | R Q N |
| M | L F I |
| F | L V I A |
| P | G |
| S | T |
| T | S |
| W | Y |
| Y | W F T S |
| V | I L M F A |

The invention also relates to a vector comprising a nucleic acid according to the invention, wherein the said nucleic acid is placed under the control of signals (i.e. a promoter, a terminator and/or an enhancer) allowing expression of the nucleic acid according to the invention. The vector may further comprise a gene for resistance to an antibiotic, such as ampicillin or kanamycin.

The term of <<vector>> designates an extrachromosomal element which may bear a non-essential gene for cell metabolism, and which generally is a circular double strand DNA. The extrachromosomal element may be a self-replicating sequence, a phage sequence or a nucleotide sequence, a single or double strand DNA or RNA, a plasmid, a cosmid. Generally, a vector contains regulatory sequences for transcription or translation, a selection marker, or a sequence allowing self-replication or chromosomal insertion. A suitable vector includes the region 5' of a gene which regulates the initiation of the transcription (i.e. a promoter) and a region 3' which controls the termination of the transcription (i.e. a terminator). The promoter may for example be that of CYC1, HIS3, GAL1, GAL10, ADH1, PGK, PHO5, GAPDH, ADC1, TRP1, URA3, LEU2, ENO, TPI, lac, trp, $\lambda P_L$, $\lambda P_R$, T7, tac, bacteriophage T5 or trc. The terminator may be derived from many genes of a preferred host cell and may optionally be omitted. Preferentially, the vector is a pQE-80L plasmid (Qiagen) containing the promoter of the T5 bacteriophage which may be induced by isopropyl-β-D-thiogalactopyranoside (IPTG).

The nucleic acids and/or the vector according to the invention may be used for transforming a cell or a host organism, i.e. for expressing or producing a protein according to the invention.

Thus, another aspect of the invention relates to a host or a host cell which contains a nucleic acid or a vector according to the invention, or which expresses (or is capable of expressing under suitable conditions) a protein according to the invention. Suitable hosts and host cells are known to one skilled in the art, and may for example be any fungus, cell or eukaryotic or prokaryotic cell line, eukaryotic or prokaryotic organisms. For example, the host or the host cell may be (i) a bacterial strain, including without being limited thereto, Gram-negative bacteria lines such as lines of *Escherichia,* for example *Escherichia coli;* of *Proteus,* for example *Proteus mirabilis;* of *Pseudomonas,* for example *Pseudomonas fluorescens;* and Gram-positive bacteria strains such as lines of *Bacilli*, for example *Bacillus subtilis* or *Bacillus brevis;* of *Streptomyces*, for example *Streptomyces lividans;* of *Staphylococcus*, for example *Staphylococcus carnosus;* and of *Lactococcus*, for example *Lactococcus lactis;* (ii) a fungal cell, including without being limited thereto, cells of the species *Trichoderma*, for example *Trichoderma reesei; Neurospora*, for example *Neurospora crassa; Sordaria*, for example *Sordaria macrospore; Aspergillus*, for example *Aspergillus niger* or *Aspergillus sojae;* or other filamentary fungi; (iii) a yeast, including without being limited thereto, cells of the species *Saccharomyces*, for example *Saccharomyces cerevisiae; Schizosaccharomyces*, for example *Schizosaccharomyces pombe; Pichia*, for example *Pichia pastoris* or *Pichia methanolica; Hansenula*, for example *Hansenula polymorpha; Kluyveromyces*, for example *Kluyveromyces lactis; Arxula*, for example *Arxula adeninivorans; Yarrowia*, for example *Yarrowia lipolytica;* (iv) an amphibian cell or cell line, such as ovocytes of *Xenopus;* (v) an insect cell or cell line, such as the lines SF9 or Sf21; (vi) a plant or a plant cell, for example a tobacco plant; and/or (vii) a mammal cell or cell line, including, without being limited thereto, CHO, BHK, HeLa, COS (i.e. COS-7) and PER.C6 cells. Preferentially, the host cell is a bacterium of the *Escherichia coli* type, and more preferentially the host cell is the strain *E. coli* BL21-Codin Plus-RI LP (Stratagene).

Another aspect of the invention relates to a method for producing a polyketide synthase, comprising the steps of:

a) cultivating a host cell according to the invention, under conditions allowing expression of a recombinant polyketide synthase, b) extracting and/or purifying said recombinant polyketide synthase.

The method further comprises a step for transforming a host cell by means of a recombinant vector as defined earlier before step a). Accordingly, the method according to the invention may comprise the steps of:

a0) transforming a host cell by means of a vector as defined earlier;

a) cultivating said transformed cell under conditions allowing expression of a recombinant polyketide synthase, b) extracting and/or purifying said recombinant polyketide synthase.

The transformation in step a0) may be carried out with methods known to one skilled in the art, for example, by transfection, electroporation, electrotransfer, microinjection, transduction, merging of cells, DEAE-dextran, precipitation with calcium phosphate, lipofection, use of a gene gun, or a DNA vector carrier (see for example, Wu et al., 1992, *J. Biol Chem.* 267:963-967; Wu et al., 1988, *J. Biol Chem.* 263: 14621-14624; Hartmut et al., Canadian patent application No. 2,012,311, published on Mar. 15, 1990). Preferably, the transformation in step a0) is carried out with a thermal shock on cells made chemically competent, in a suitable culture medium. Preferably, the thermal shock is carried out between 35° C. and 50° C. for 30 seconds to 1 min followed by a return into ice for 1 to 3 min. Still more preferably, the thermal shock is achieved at 42° C. for 45 seconds followed by a return into ice for 2 min. By suitable culture medium, is meant is a culture medium allowing the growth of transformed cells. Such a culture medium is known to one skilled in the art. For example, this is a medium including, without being limited thereto, a carbonaceous substrate or a source of carbon which may be metabolized by the transformed cell. The carbonaceous substrate or the source of carbon may be selected from monosaccharides, oligosaccharides, polysaccharides, simple-carbon substrates, and a mixture of these compounds. Optionally, the culture medium contains an antibiotic, such as ampicillin or kanamycin.

Preferably, the cell transformed in step a0) is a bacteria of the *E. coli* type such as the strain *E. coli* BL21-CodinPlus-RILP (Stratagene), transformed with a vector and/or a nucleic acid according to the invention, and cultivated by using a suitable medium, such as the Luria-Broth (LB) medium, preferably containing at least 100 μg/ml of ampicillin.

The culture made in step a) has the purpose of allowing expression of the recombinant polyketide synthase. It may be made by methods known to one skilled in the art, for example by means of a bio-reactor, also called a fermenter. The bio-reactor is a hermetically sealed tank provided with a stirring system, a ventilation system, with probes being used for measuring various parameters (pH, temperature, dissolved oxygen) and supply pores allowing accurate dosage of the composition of the culture medium during fermentation. The fermentation in the bio-reactor is carried out in two phases: a growth phase I during which the cells divide at an accelerated rate, and then an accumulation or induction phase II leading to the expression of the recombinant protein. One skilled in the art is able to determine the suitable culture conditions for allowing the growth phase I and the accumulation or induction phase II. In a particular embodiment, the phases I and II may be made as described in Example 1.3.

The extraction and/or the purification in step b) may be carried out by means of methods known to one skilled in the art. As a non-limiting example, the extraction may be achieved by lysis of the cells by means of a French press, by sonication, or via an enzymatic route, or with any other standard technique. The lysis of the cells may be followed by a filtration step, and/or centrifugation of the lysate. As a non-limiting example, the purification may be achieved by means of chromatography (on or ion exchange column affinity or size-separation), centrifugation, differential solubility or by any other standard technique. In a particular embodiment, the extraction and/or the purification may be achieved as described in Example 1.3.

Preferably, said production method allows production of at least 1 mg/L to 20 mg/L of pure protein, and still preferably at least 5 to 10 mg/L of pure protein.

Method for Producing Polyphenol Compounds

The inventors have thus identified that a polyketide synthase of type III (PKSIII) extracted from a brown alga was capable of synthesizing phloroglucinol and/or one of its derivatives from diverse carbonaceous substrates, and more particularly from malonyl-CoA.

The present invention therefore also relates to a method for producing at least one polyphenol compound, wherein:

a polyketide synthase of type III (PKSIII) of brown alga is put into contact with at least one carbonaceous substrate under conditions allowing majority production of at least one polyphenol compound, said produced phenol compound is phloroglucinol and/or one of its derivatives.

Preferably, the method includes a step for recovering the phloroglucinol and/or one of its derivatives. This recovery step may comprise an extraction step and/or a purification step.

By <<polyphenol compound>>, is meant a compound stemming from the secondary metabolism of the plant kingdom, i.e. land plants and aquatic macrophytes, which have at least one aromatic ring with 6 carbons (phenol), itself bearing one or several hydroxyl functions (OH). Many families of molecules are distinguished, for which the structure is relatively close: flavonoids (yellow-orangey plant pigments), anthocyans (compounds with red to violet colors responsible for the purple color of red grapes) and tannins.

By <<polyketide synthase of type III>>, is meant an enzyme capable of synthesizing phloroglucinol and/or one of its derivatives from a carbonaceous substrate. Preferably, PKSIII is obtained from a brown marine alga, still preferably, PKSIII is obtained from brown marine algae of the *Ectocarpus* genus, and still more preferably, PKSIII stems from the brown marine alga *Ectocarpus siliculosus*.

In a preferred embodiment, PKSIII is produced by the method according to the invention described above.

According to a particular aspect of the invention, PKSIII comprises or consists in a protein according to the invention. More particularly, PKSIII comprises or consists in the sequence SEQ ID NO: 1 or SEQ ID NO: 3 or a sequence having at least 93%, 95% or 99% identity with the sequence SEQ ID NO: 1 or SEQ ID NO: 3.

The sequence having at least 93% identity with SEQ ID NO: 1 or SEQ ID NO: 3 may differ from the reference sequence (i.e. SEQ ID NO: 1 or SEQ ID NO: 3) by one or several conservative substitution(s). The terms of <<conservative substitutions>> are as defined above.

According to a particularly preferred aspect, PKSIII consists in the sequence SEQ ID NO: 1 or SEQ ID NO: 3.

According to another particular aspect of the invention, said PKSIII comprises or consists in a sequence which may be coded by the nucleotide sequence SEQ ID NO: 2 or a sequence having at least 85%, 90%, 91%, 92%, 93%, 94%, 95%, or 99% identity with SEQ ID NO: 2.

According to another particular aspect of the invention, said PKSIII comprises or consists in a sequence which may be coded by the nucleotide sequence SEQ ID NO: 4 or a sequence having at least 85%, 90%, 91%, 92%, 93%, 94%, 95%, or 99% identity with SEQ ID NO: 4.

The sequence having at least 85% identity with SEQ ID NO: 2 or SEQ ID NO: 4 may differ from the reference sequence (i.e. SEQ ID NO: 2 or SEQ ID NO: 4) by one or several conservative substitution(s). The terms of <<conservative substitutions>> are as defined above.

By <<carbonaceous substrate>>, is meant a compound used as a source of carbon. For example, the carbonaceous substrate includes compounds of the metabolite type, such as $C_1$-$C_{18}$ carbon chains, fatty acids, mono-, di-, tri-glycerides, polyols, phospholipids, phosphoacids, monosaccharides, amino acids, nucleotides, hydrolyzable homo- or hetero-oligomers or polymers of these compounds, and the biologically active forms of these compounds. Said metabolites may be of any biological or synthetic origin. Other examples of compounds are aromatic, aliphatic and cycloaliphatic $C_1$-$C_{18}$ compounds.

In a particular aspect, the carbonaceous substrate is selected from malonyl-CoA, acetyl-CoA, hexanoyl-CoA, decanoyl-CoA, lauroyl-CoA, and/or palmitoyl-CoA.

In a particularly preferred embodiment, the carbonaceous substrate is malonyl-CoA.

By <<phloroglucino>>, is meant benzene-1,3,5-triol, its CAS number is 108-73-6.

By <<derivative of phloroglucinol>>, are notably meant the following compounds: acetyl-phloroglucinol, lauroyl-phloroglucinol, palmitoyl-phloroglucinol, hexanoyl-phloroglucinol, decanoyl-phloroglucinol.

In a particularly preferred aspect, the carbonaceous substrate is malonyl-CoA and the produced phenol compound consists in or comprises phloroglucinol.

In another particularly preferred aspect, the carbonaceous substrate is malonyl-CoA and acetyl-CoA, and the produced phenol compound consists in or comprises phloroglucinol and acetyl-phloroglucinol.

In another particularly preferred aspect, the carbonaceous substrate is malonyl-CoA and lauroyl-CoA and the produced phenol compound consists in or comprises phloroglucinol and lauroyl-phloroglucinol.

In another particularly preferred aspect, the carbonaceous substrate is malonyl-CoA and palmitoyl-CoA and the produced phenol compound consists in or comprises phloroglucinol and palmitoyl-phloroglucinol.

In another particularly preferred aspect, the carbonaceous substrate is malonyl-CoA and hexanoyl-CoA and the produced phenol compound consists in or comprises phloroglucinol and hexanoyl-phloroglucinol.

In another particularly preferred aspect, the carbonaceous substrate is malonyl-CoA and decanoyl-CoA and the produced phenol compound consists in or comprises phloroglucinol and decanoyl-phloroglucinol.

By majority production of phloroglucinol or one of its derivatives, is meant that the phloroglucinol or one of its derivatives is the product which is found in the highest concentration relatively to the other produced compounds. Preferentially, the production of phloroglucinol or one of its derivatives is of at least 30%, 40%, 50%, 60%, 70%, 80%, 90% or 100%.

The step for putting the polyketide synthase in contact with at least one carbonaceous substrate is known to one skilled in the art. Preferably, but in a non-limiting way, this step is carried out as described in Examples 1.4 or 1.5. More particularly, it comprises the steps of (i) putting the polyketide synthase in contact with the carbonaceous source in a suitable medium, (ii) incubating the thereby obtained mixture.

The suitable medium in step (i) may be a HCl-EDTA medium, for which the respective concentrations are comprised between 30 and 70 mM of HCl and 0.5 and 2 mM of EDTA, preferentially comprising between 45 and 55 mM of HCl and 0.8 and 1.2 mM of EDTA, even more preferentially the HCl and EDTA concentrations are 50 mM and 1 mM, respectively. Preferably, the pH of the medium is comprised between 6 and 8, and still preferably, the pH is of about 7.5.

The incubation (ii) is preferably carried out at room temperature, i.e. at a temperature comprised between 20° C. and 30° C., and for a duration comprised between 30 mins and 8 hrs. Still preferably, the incubation is carried out at a temperature comprised between 22° C. and 28° C., and still preferably the incubation is carried out at about 25° C. Preferably, the incubation is carried out for a duration comprised between 1 hr and 5 hrs, and still preferably the incubation is carried out for about 1 hr, 2 hrs, 3 hrs, 4 hrs or 5 hrs. In a particularly preferred embodiment, the incubation is carried out at about 25° C. for about 1 hr, 2 hrs, 3 hrs, 4 hrs or 5 hrs.

The extraction and/or purification step may be carried out with techniques known to one skilled in the art. For example, the extraction may be achieved by means of ethyl acetate. The purification step may for example be achieved by chromatography on a thin layer (TLC) or by gas chromatography coupled with mass spectrometry (GC-MS).

The polyphenol compounds produced by the method according to the invention, such as phloroglucinol and its derivatives, may be used in many applications in the pharmaceutical, nutraceutical, cosmetic, agri-feed or plant protection fields.

Thus, the invention also relates to a method for producing a pharmaceutical, nutraceutical, cosmetic, agri-feed or plant protection compound, said method comprising the steps of:

a) producing at least one polyphenol compound by the method according to the invention;

b) optionally modifying said phenol compound obtained in step a) for producing a pharmaceutical, nutraceutical, cosmetic, agri-feed or plant protection compound, c) adding a support, carrier, excipient, diluant and/or adjuvant which are acceptable for the retained application.

The invention also relates to the use of the polyphenol compounds produced by the method according to the invention for preparing pharmaceutical, nutraceutical, cosmetic, agri-feed or plant protection compositions.

The object of the invention is also these compositions.

More particularly, the pharmaceutical or nutraceutical compositions may contain supports or the like (carriers, excipients, diluents) and/or adjuvants which are pharmaceutically acceptable. Used herein, the term of "pharmaceutically acceptable" preferably means approved by a government regulatory agency, in particular recommended in the American or European Pharmacopoeia, for a use in animals, and more particularly in humans. Suitable pharmaceutical supports or the like are notably described in "Remington's Pharmaceutical Sciences" by E. W. Martin.

These pharmaceutically acceptable supports or the like may be sterile liquids, such as water and oils, including liquids derived from petroleum, animals, plants, or of synthetic origin, such as groundnut oil, soya bean oil, mineral oil, sesame oil, and other similar oils. Water is a preferred support when the pharmaceutical composition is administered via an intravenous route. Saline solutions and aqueous solutions of dextrose and glycerol may also be used as liquid supports, in particular for injectable solutions. Suitable pharmaceutical excipients comprise mannitol, human serum albumin (HSA), starch, glucose, lactose, saccharose, gelatin, malt, rice, flour, chalk, silica gel, magnesium carbonate, magnesium stearate, sodium stearate, glycerol monostearate, talcum, sodium chloride, powdered skimmed milk, glycerol, propylene, glycol, water, ethanol and other similar excipients. These compositions may assume the form of solutions, suspensions, tablets, pills, capsules, powders, formulations with prolonged release or other similar forms.

These compositions will contain a diagnostic or therapeutic effective amount of the active compound with a suitable amount of the support or the like so as to provide a form for a suitable administration to the patient. Although intravenous injection is a highly efficient administration form, other methods may be used, such as an injection, or nasal or parenteral administration.

More particularly, cosmetic compositions may contain a cosmetically acceptable carrier. By "cosmetically acceptable carrier", is meant a carrier suitable for use in contact with human and animal cells, in particular the cells of the epidermis, without any toxicity, irritation, induced allergic response or the like, and in proportion with an advantage/reasonable risk ratio. As an example of a cosmetically acceptable carrier, mention may notably be made of water, in particular distilled water.

The cosmetic compositions according to the invention may further comprise any additive customarily used in the cosmetic field, such as sequestering agents, anti-oxidants, preservatives, fillers, electrolytes, humectants, coloring agents, usual bases or acids, either mineral or organic, perfumes, essential oils, cosmetic actives, moisteners, vitamins, essential fatty acids, sphingolipids, self-tanner compounds, skin soothing and protective agents. Of course, one skilled in the art will make sure that he/she selects this or these optional complementary compounds and/or their amount, such that the advantageous properties of the composition according to the invention are not or substantially not altered. These additives may be present in the composition in an amount from 0.001% to 20% by weight based on the total weight of the composition.

In a known way, the cosmetic compositions of the invention may contain customary adjuvants in the cosmetic or dermatological field, such as emulsifiers, hydrophilic or lipophilic gelling agents, hydrophilic or lipophilic actives, preservatives, anti-oxidants, perfumes, fillers, filters and coloring materials. The amounts of these different adjuvants are those conventionally used in the cosmetic and/or dermatological fields and, for example are from 0.01% to 20% of the total weight of the composition. These adjuvants, depending on their nature, may be introduced into the fatty phase, into the aqueous phase and/or into the lipid vesicles.

The application of a cosmetic composition according to the invention is carried out via a topical route on the skin, including the mucosas, notably the lips or appendages. The application of a cosmetic composition according to the invention may also be carried out by intradermal injection.

The cosmetic compositions according to the invention may appear in all the galenic forms normally used for topical application, in the form of an ointment, a cream, an oil, a milk, a pomade, a powder, a swab, a solution, a gel, a spray, a lotion, a suspension, a soap.

The compositions of the invention may be cosmetic compositions in the form of an oil-in-water or water-in-oil emulsion, or a multiple emulsion, a microemulsion, a hydroalcohol gel, a cream, an oil, a hydroalcohol lotion.

The cosmetic compositions of the invention are particularly useful, for moistening, soothing, repairing and/or protecting the skin.

These cosmetic compositions are also particularly advantageous for controlling skin aging i.e. notably the phenomena of wrinkles, loss of tonicity and elasticity due to structural modifications of the skin due to aging.

The cosmetic compositions of the invention are also useful for protecting the skin from exterior aggressions, such as notably ultraviolet rays or air contaminations.

The plant protective compositions according to the invention may further comprise one or several surfactants, preservatives, dispersants, wetting agents, emulsifiers, anti-foam agents, water.

The plant protective compositions according to the invention may be formulated in different forms, for example in the form of wettable powders, dispersible granules, concentrated suspensions, powders for powdering.

The invention also relates to the use of phloroglucinol and/or one or several of its derivatives produced by the method according to the invention for treating spasmodic disorders, viral diseases, parasite diseases, microbial diseases, fungal diseases, dermatological disorders, hypertension, osteoporosis, inflammatory diseases, vascular diseases, sexual disorders, cancers, diabetes, neurodegenerative diseases, depression and allergy.

The invention also relates to methods for treating spasmodic disorders, viral diseases, parasite diseases, microbial diseases, fungal diseases, dermatological disorders, hypertension, osteoporosis, inflammatory diseases, vascular diseases, sexual disorders, cancers, diabetes, neurodegenerative diseases, depression and allergy, comprising the administration of phloroglucinol and/or of one or several of its derivatives to a patient in need thereof.

Spasmodic disorders may notably comprise functional disorders of the digestive tract (colitises) and of bile ducts, renal or hepatic colics, gynecological pains, and contractions during pregnancy.

Viral diseases may notably comprise infections with the acquired human immunodeficiency virus (HIV) and with the virus of herpes.

The parasite diseases may notably comprise malaria.

Microbial diseases may notably comprise infections due to Gram-negative or Gram-positive bacteria, and more particularly the bacteria of the types *Streptococcus mutans, Porphyromonas gingivalis, Bacillus subtilis* and *Staphylococcus aureus*.

The fungal diseases may notably comprise infections due to *Aspergillus niger, Aspergillus flavus, Mucor* and *Cladosporium*.

Dermatological disorders may notably comprise psoriasis, skin alopecia, skin healing problems, and skin aging i.e. notably the phenomena of wrinkles, loss of tonicity and elasticity due to structural modifications of the skin due to aging.

Vascular diseases may notably comprise Raynaud's disease and acrocyanosis.

Neurodegenerative diseases may notably comprise Alzheimer's disease, Kiloh Nevin's syndrome, carpal tunnel syndrome, Tardy Ulnar's paralysis, Guyon's canal syndrome.

Sexual disorders may notably comprise erection disorders.

Phloroglucinol or its derivatives may be used alone or in a combination with other compounds having a therapeutic activity for treating the disorders mentioned above.

The invention will be explained in more detail with the following examples, without limiting the scope thereof.

EXAMPLES

Example 1

Equipment, Experimental Methods and Procedures 1.1. Chemical Products

The compounds malonyl-CoA, acetyl-CoA, hexanoyl-CoA, lauroyl-CoA, palmitoyl-CoA and decanoyl-CoA are from Sigma. The [$2^{-14}$C] Malonyl-CoA (55 mCi/mmol) is from Perkin Elmer (USA).

1.2. Bacterial Strain

The strain *Escherichia coli* DH5a [fhuA2 _(argF-lacZ) U169 phoA glnV44 Φ80 _(lacZ)M15 gyrA96 recA1 relA1 endA1 thi-1 hsdR17] (Stratagene) was used as a host strain for maintaining plasmids. For protein expression, the <<cis-repressed>> pQE-80L derivatives were transformed into the strain *E. coli* BL21 (DE3) codon Plus RILP [*E. coli* B F– ompT hsdS(rB– mB–) dcm+ Tetr gal I (DE3) endA Hte [argU ileY leuW Camr]] (Stratagene) containing additional copies of the tRNA arginine, isoleucine, proline and leucine.

1.3. Expression and Purification of the Recombinant Polyketide Synthase of Type III of *Ectocarpus Siliculosus*

The gene coding for the PKS1 of *E. siliculosus* was amplified by PCR (30 amplification cycles) from the cDNA described in Cock et al., 2010, *Nature* 465(7298): 617-621. The expression vector pQE-80L (Qiagen) containing the promoter of the bacteriophage T5 inducible by isopropyl-b-D-thiogalactopyranoside (IPTG) was used for expressing the protein (FIG. 1). The PKS1 of *E. siliculosus* was cloned in the vector at the restriction sites SphI and HindIII by using the oligonucleotides PQECHSFowBis (5'-GGCGGATCCG-CATGCATGTCCAAGGACGAGCAGACGGTATAC-CCGGTCATCGCC-3' (SEQ ID NO: 11)) and PQECHSRev (5'-GGCTAAGCTTTTACTAGATCTGCCT-GAGAAGGATGCCCTCTGCCCC-3' (SEQ ID NO: 12)). The PCR conditions used for the cloning are the following: 50 ng of DNAc PKS1, 0.4 µM of each oligonucleotide, 0.4 mM of dNTP mix in a reaction medium of 50 µL with the Phusion enzyme (Finnzyme) with its HF buffer according to the recommendations of the supplier. The reaction was carried out in 3 steps: denaturation of the DNA and of the primers at 98° C. for 5 min, 30 PCR cycles at 98° C. for 30 s, 52° C. for 30 s, 72° C. for 2 min and then finally an elongation end step at 72° C. for 7 min. An additional step consisting of adding dAs to the ends of the fragment from the PCR was carried out for 10 min at 72° C. with addition of 0.5 µL of GoTaq enzyme (Promega). The amplified DNA fragment is directly purified on a MinElute column (Qiagen). Ligation is carried out in a first phase in pGEM-Teasy (Promega) according to standard conditions (one night at room temperature in a 12 µL reaction medium containing a product to be cloned/vector with the T4 DNA ligase of the Promega kit ratio 10/1). The ligation product is introduced by a thermal shock into competent cells DH5alpha prepared in the laboratory, and a transformant is selected for mass production of a recombinant vector containing the PKS1 insert. The plasmid is purified with the Miniprep SV kit (Promega). After checking the nucleotide sequence of PKS1, the insert is digested by SphI and HindIII, and then purified on agarose gel with the MinElute kit (Qiagen) before being ligated into the vector pQE80L (Qiagen) doubly digested with the same restriction enzymes and dephosphorylated by SAP (NE Biolabs). The ligation conditions in pQE80L are the same as described earlier.

The constructs code for a total protein to which a label of six histidines (His-tag) was added to its N-terminal end. The constructs were transformed into the strain *E. coli* BL21-CodonPlus-RILP strain (Stratagene) by using a solid LB medium containing 100 µg/mL of ampicillin. The expression of the recombinant protein was achieved by cultivating the bacteria in a ZYP medium at 20° C. by using a 5 L fermenter batch. After 48 hours of cultivation, induction of the protein expression is continued by adding 0.5 mM of IPTG. After this last induction, the cells are collected by centrifugation and frozen to −80° C.

The cells are then re-suspended in the medium A (20 mM Tris-HCl pH 7.5, 300 mM NaCl and 50 mM Imidazole) supplemented with a mixture of a protease inhibitor, of the lysozyme (1 mg/mL) and of the DNase (10 mg/ml). The lysis of the cells is then carried out with two passes into a French press in order to reduce the viscosity of the supernatant. The cell debris are removed by centrifugation at 20,000 rpm at 4° C. for 1 hr 30 mins. The supernatant is then transferred into an Ni-sepharose column (GE Healthcare). The cell extract is then fractionated by affinity chromatography, so called <<IMAC>> (Immobilized-metal affinity chromatography) on an ÄKTA™-Avant apparatus (GE Healthcare). After a washing step with a buffer A (20 mM Tris-HCl pH 7.5; 300 mM NaCl; 50 mM imidazole), the proteins are eluted according to a procedure with a gradient from 50 mM to 500 mM of imidazole by mixing the buffer A with the buffer B (20 mM Tris-HCl pH 7.5; 300 mM NaCl; 500 mM imidazole). The fractions C12 to E10 were then concentrated to 5 ml by ultrafiltration on a 10 kDa CentriPrep (Millipore) and simultaneously exchanged in a buffer containing 20 mM of Tris-HCl, pH 7.5 100 mM NaCl.

The proteins were then transferred into a filtration column on a Superdex S-200 HR 16/60 gel (GE Healthcare) and purified by steric exclusion chromatography by using an ÄAKTA-Avant apparatus (GE Healthcare). The purity and the integrity of all the protein samples were analyzed by electrophoresis on a 12% SDS-polyacrylamide gel and by MALDI-TOF mass spectrometry.

1.4. Enzymatic Tests (Thin Layer Chromatography (TLC))

The enzymatic tests were carried out by using:
a) Malonyl-CoA alone: 200 μM of malonyl-CoA was added to the test mixture containing 20 μM of malonyl-CoA radio-labelled with $[^{2-14}0]$ (55 mCi/mmol), 50 μg of purified recombinant enzyme PKS1 of E. siliculosus, in a final volume of 500 μl of 50 mM Tris HCl pH 7.5 and 1 mM of EDTA, or
b) the five following substrates: acetyl-CoA, hexanoyl-CoA, lauroyl-CoA, palmitoyl-CoA and decanoyl-CoA. 200 μM of each substrate was added to the test mixture containing 20 μM of malonyl-CoA radio-labelled with $[^{2-14}C]$ (55 mCi/mmol), 50 μg of purified recombinant enzyme PKS1 of E. siliculosus, in a final 500 μl volume of 50 mM Tris HCl pH 7.5 and 1 mM of EDTA.

The incubation of the mixtures in a) and b) was carried out at room temperature for 1 hr or 3 hrs and was stopped by adding 37% HCl. The products of the reactions were then extracted with 1 ml of ethyl acetate, and separated by thin layer chromatography (Merck Art. 1.11798 Silica gel 60 F254; ethyl acetate/hexane/AcOH 65:25:5, v/v/v).

The radioactive signals were detected and quantified by means of a Typhoon imaging system (Molecular Dynamics-GE Healthcare).

1.5. Enzymatic Tests (Mass Spectrometry Coupled with Gas Chromatography (GC-MS))

The enzymatic tests were carried out by using:
a) Malonyl-CoA alone: 200 μM of malonyl-CoA was added to the test mixture containing 50 μg of purified recombinant enzyme PKS1 of E. siliculosus, in a final 500 μl volume of 50 mM Tris HCl, pH 7.5 and 1 mM of EDTA, or
b) the five following substrates: acetyl-CoA, hexanoyl-CoA, lauroyl-CoA, palmitoyl-CoA and decanoyl-CoA. 200 μM of each substrate was added to the test mixture containing 20 μM of malonyl-CoA, 50 μg of purified recombinant enzyme PKS1 of E. siliculosus, in a final 500 μl volume of 50 mM Tris HCl pH 7.5 and 1 mM of EDTA.

The incubation of the mixtures in a) and b) was carried out at room temperature for 1, 2, 3, 4, or 5 hrs and was stopped by adding 37% HCl. The products of the reactions were then extracted with 1 ml of ethyl acetate. 2.50 μg of vanillin were added as an internal standard. The samples were then vortexed for 5 mins and centrifuged for 5 mins at 1,000 G. The organic phase was transferred into a glass flask and evaporated under a nitrogen flow. Trimethylsilyl-ethers (TMS-ether) were formed by adding 100 μl of acetonitrile and 100 μl of Sylon-BFT for 60 min at 60° C. and evaporated under a nitrogen flow. The metabolites were re-suspended in a 100 μl of hexane and analyzed by GC-MS in an EI mode on an Agilent GC 6890 coupled with a detector <<5973 MS Detector>> (Agilent, Les Ulis, France) and equipped with a DB-5MS column (30 m×0.25 mm of internal diameter×0.25 μm of film thickness (J and W Scientific, Agilent)). The temperatures of the injection orifice and of the interface are 250 and 280° C. respectively; that of the ion source and of the MS analyser were respectively set to 230 and 150° C. The samples were injected in a <<division-less injection>> mode or a <<splitless>> mode. The temperature of the oven was first set to 60° C. for 5 min, and then increased by 10° C./min up to 100° C., raised at a rate of 1° C./min up to 150° C. and finally raised at a rate of 8° C./min up to 290° C., and then maintained for 5 mins. The compounds were ionized by impacts of electrons with an energy of 70 eV. The analytes were detected by a total ion current of 50 to 850 m/z. All the data were processed with the MSDchem software package (EMBL-EBI).

1.6. Enzymatic Tests (Mass Spectrometry Coupled to Liquid Chromatography (LC-MS))

The enzymatic tests were carried out by using:
a) Malonyl-CoA alone: 200 μM of malonyl-CoA were added to the test mixture containing 50 μg of purified recombinant enzyme PKS1 of E. siliculosus, in a final 500 μl volume of 50 mM Tris HCl pH 7.5 and 1 mM of EDTA, or
b) the five following substrates: acetyl-CoA, hexanoyl-CoA, lauroyl-CoA, palmitoyl-CoA and decanoyl-CoA. 200 μM of each substrate were added to the test mixture containing 20 μM of malonyl-CoA, 50 μg of purified recombinant enzyme PKS1 of E. siliculosus, in a final 500 μl volume of 50 mM Tris HCl pH 7.5 and 1 mM of EDTA.

The incubation of the mixtures in a) and b) was carried out at room temperature for 1, 2, 3, 4, or 5 hrs and was stopped by adding 37% HCl. The products of the reactions were then extracted with 1 ml of ethyl acetate. 2.50 μg of vanillin were added as an internal standard. The samples were then vortexed for 5 mins and centrifuged for 5 min at 1,000 G. The organic phase was transferred into a glass flask and evaporated under a nitrogen flow. The metabolites were re-suspended in 100 μl of hexane. For LC-MS analysis, a liquid chromatography system DionexUltiMate 3000Rapid Separation LC (RSLC, Dionex) is coupled with a hybrid mass spectrometer LTQ-Orbitrap™ (Thermo Fisher Scientific). All the solvents and reagents used are of an analytical grade or HPLC grade (Carlo Erba). The chromatographic separation was achieved on a column Acclaim RSLC 120, C18, 2 μm particle size, 2.1×100 mm column (Dionex) maintained at 20° C. The mobile phase is water containing 0.1% of acetic acid (A) and acetonitrile containing 0.1% of acetic acid (B). The flow was adjusted to 0.25 ml.min$^{-1}$. The elution gradient (A:B, v/v) was produced as described in the following: 80:20 from 0 to 1 min; and then 0:100 from 1 to 10 mins; and then 20:100 for 10 mins and for 20.1 mins, 80:20 for 10 mins. The injected volume is 50 μL. The HPLC column was connected without uncoupling with the electrospray operative interface in a negative mode. The voltage of the spray was 3.5 kV and the temperature of the transfer capillary was maintained to 350° C. The "sheath liquid" and the auxiliary nitrogen gas were applied for assisting evaporation of the solvent at a flow of 25 and 5 arbitrary units respectively. The totality of the scans of the mass spectra was obtained for m/z from 50 to 2,000 by using a mass resolution of 30,000 FWHM at 400 m/z in a profile mode.

Example 2

Results 2.1. Nucleotide and Protein Sequences of PKS1

The gene PKS1 present on the genome of E. siliculosus has been available in public data bases since June 2010 and it corresponds to a sequence of 1,245 nucleotides, coding for a protein with 415 amino acids. An addressing signal peptide was predicted according to the use of the SIGNALP v.2.0 software package which uses the two Neural Networks and Hidden Markov models (Nielsen et al., *Protein Eng*, 1999, 12: 3-9) and this sequence of 102 nucleotides, corresponding to the first 34 amino acids was removed in order to obtain a mature recombinant protein expressed in the bacterial cytoplasm.

2.2. Over-Expression in *E. Coli* and Purification of the Recombinant PKS1

According to the procedures for over-expression and purification of PKS1 in *E. coli*, the gel for electrophoresis of the elution fractions from the affinity column <<IMAC>> stained with Coomassie blue allows detection of the production of a recombinant protein at the expected size of about 50 kDa. In order to increase the purity level of the recombinant protein and remove the inactive forms of the enzyme (e.g. soluble aggregates), a second purification on a size exclusion column gave the possibility of obtaining the recombinant protein with a homogeneity of more than 99% according to DLS (Dynamic Light Scattering) analysis. This analysis coincides with the elution volume of the protein on a filtration gel and suggests that the active form of the enzyme is actually a dimer like the majority of the PKSIIIs known to this day. The purity of the enzyme was also validated by MALDI-TOF mass spectrometry analysis of the cut-out band on a gel and digested with trypsin. The masses of the obtained fragments actually correspond to the sequence of PKS1 with 32 identified peptides corresponding to 47% coverage of the sequence (FIG. 2).

The production yield for a culture in a 5 L fermenter was estimated to be about 5 to 10 mg of active recombinant protein per liter of culture and may therefore support an industrial production level. Further, the enzyme proved to be stable for one to two months at 4° C. and it supports freezing to −80° C.

2.3. Enzymatic Activity: Mass Spectrometry Analyses of the Formed Compounds

Figure 3:
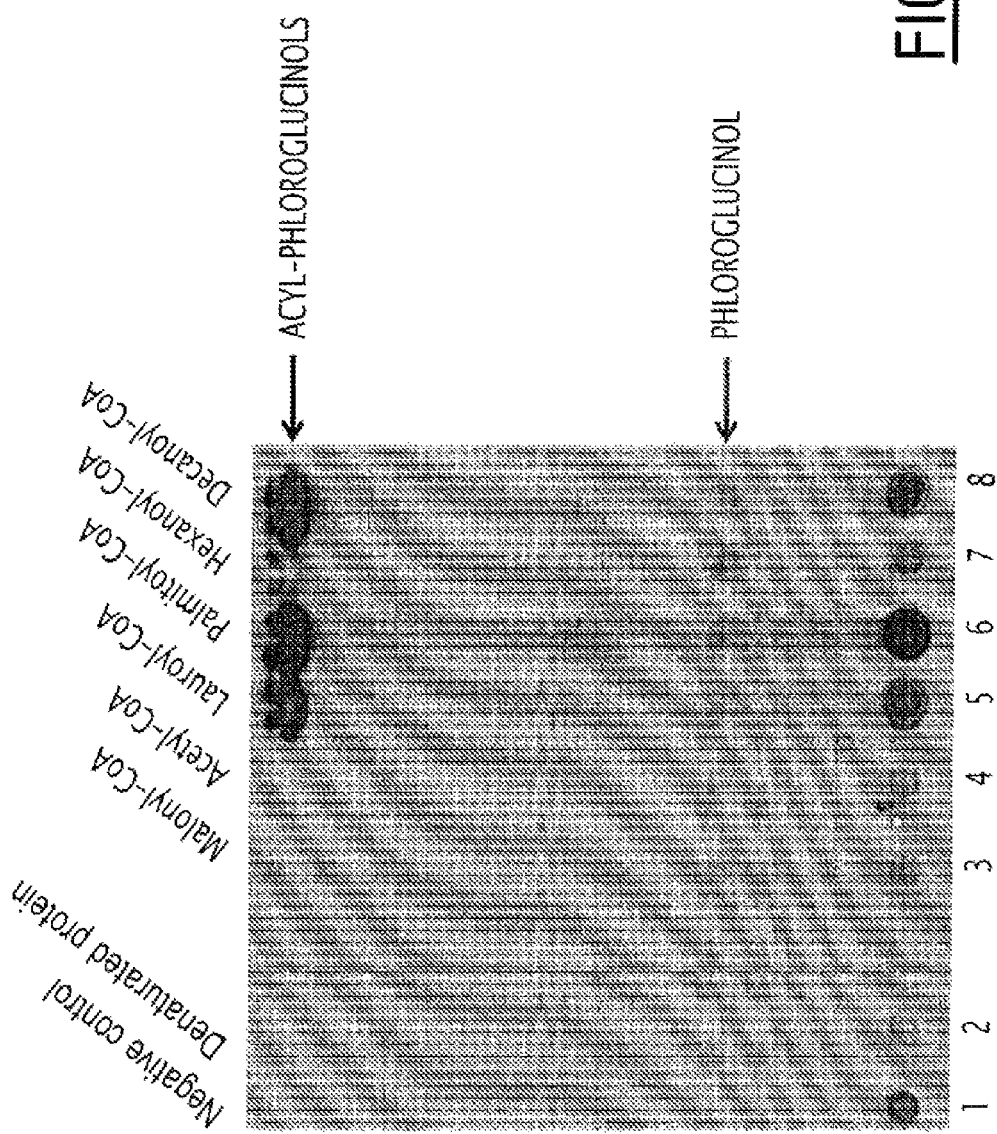
FIG. 3. represents the thin layer chromatography analysis of the products formed during the enzymatic reaction using the following different substrates: malonyl-CoA alone, malonyl-CoA+acetyl-CoA, malonylCoA+hexanoyl-CoA, malonyl-CoA+lauroyl-CoA, malonyl-CoA+palmitoyl-CoA and malonyl-CoA+decanoyl-CoA.

The analysis of the products formed in TLC indicate that there is formation of phloroglucinol with or without starters (malonyl-CoA alone, malonyl-CoA+acetyl-CoA, malonyl-CoA+hexanoyl-CoA, malonyl-CoA+lauroyl-CoA, malonyl-CoA+palmitoyl-CoA and malonyl-CoA+decanoyl-CoA) and that the main obtained compounds of the reaction are phloroglucinol in the case of malonyl-CoA alone or of malonyl-CoA+acetyl-CoA and an acyl-phloroglucinol in the case of the malonyl-CoA with the other starters (acetyl-CoA, hexanoyl-CoA, lauroyl-CoA, palmitoyl-CoA and decanoyl-CoA) (FIG. 3).

Figure 4:
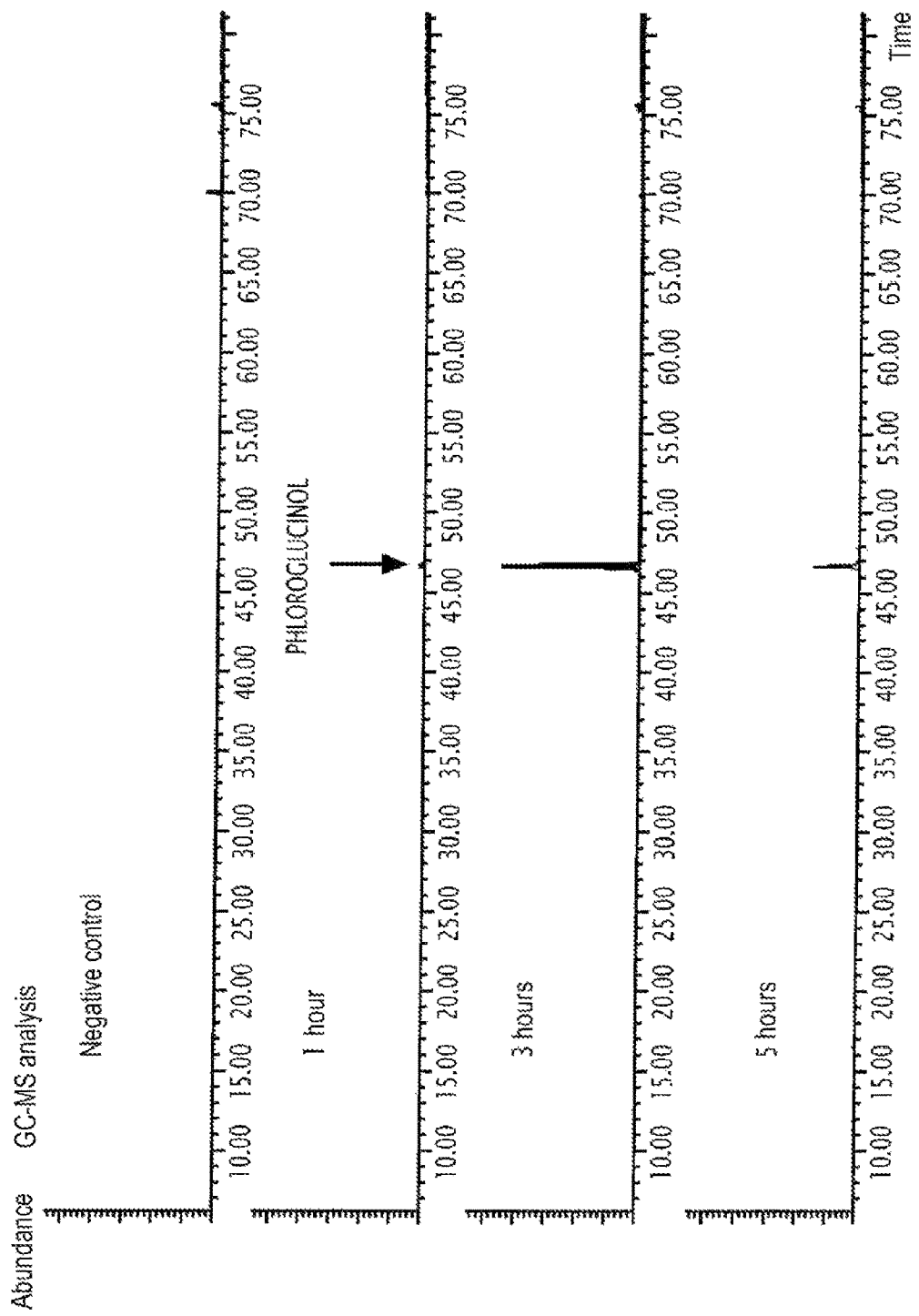
FIG. 4. represents the GC-MS mass spectrometry analysis of the products formed during the enzymatic reaction using the following different substrates: malonyl-CoA alone, malonyl-CoA+acetyl-CoA, malonylCoA+hexanoyl-CoA, malonyl-CoA+lauroyl-CoA, malonyl-CoA+palmitoyl-CoA and malonyl-CoA+decanoyl-CoA.
Figure 5:
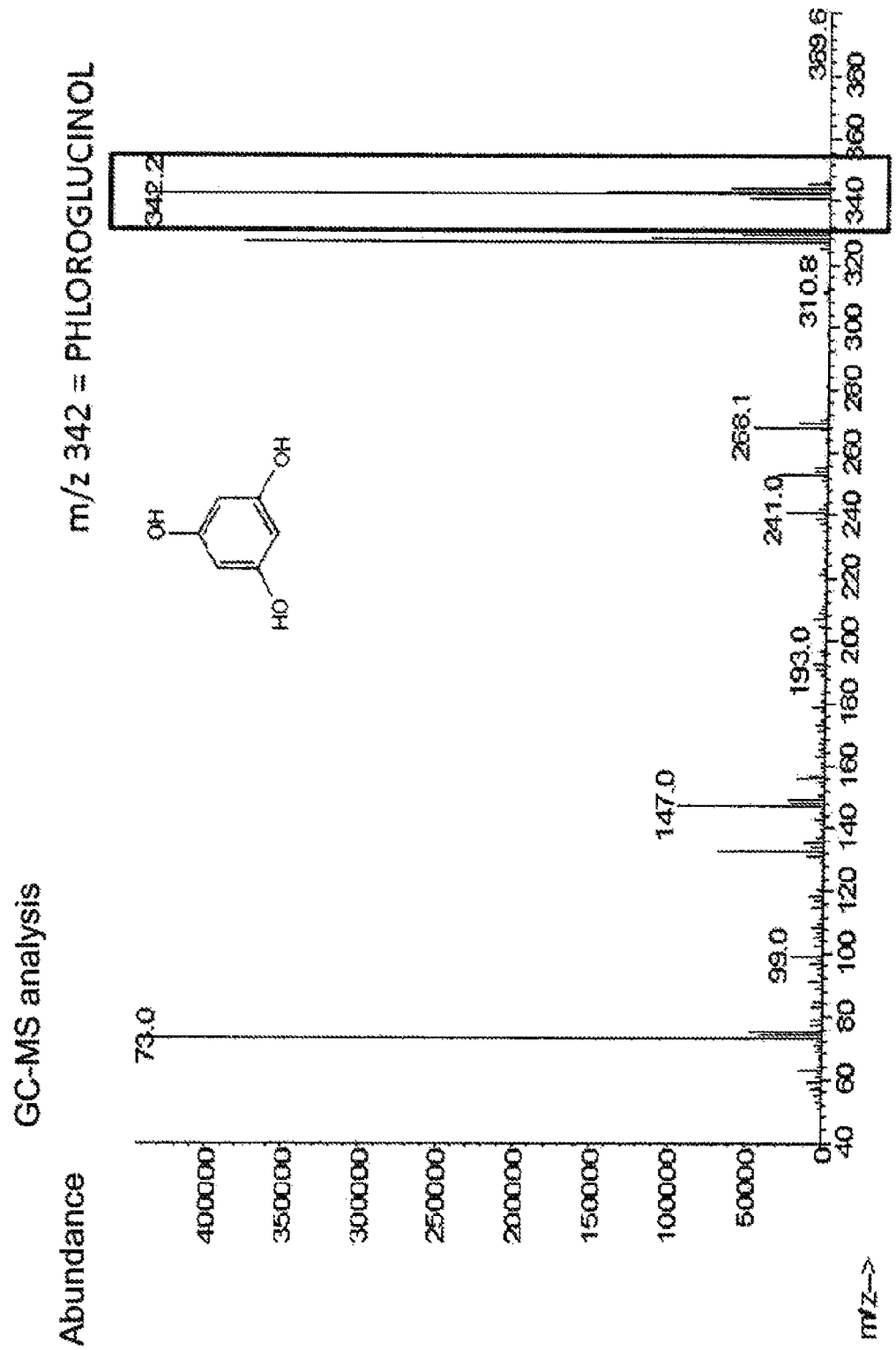
FIG. 5. represents the GC-MS mass spectrometry analysis of the products formed during the enzymatic reaction using the following different substrates: malonyl-CoA alone, malonyl-CoA+acetyl-CoA, malonyl-CoA+hexanoyl-CoA, malonyl-CoA+lauroyl-CoA, malonyl-CoA+palmitoyl-CoA and malonyl-CoA+decanoyl-CoA.

These results were confirmed by GC-MS mass spectrometry analysis which allowed clear identification of the production of phloroglucinol from malonyl-CoA with a production optimum located between 3h and 5h of reaction time (FIGS. 4 and 5 and Table 5).

TABLE 5

Amount of phloroglucinol produced by PKS1 from Malonyl-CoA.

| Time (h) | Area m/z 194 | Area m/z 342 | Ratio 342/194 | Phloroglucinol/ sample (µg) |
|---|---|---|---|---|
| CB | 6232490 | 0 | 0 | 0.00 |
| 1 | 5968432 | 955510 | 0.16009397 | 1.70 |
| 2 | 6169748 | 5641093 | 0.91431498 | 9.08 |
| 3 | 5847716 | 39184281 | 6.70078386 | 65.64 |
| 4 | 4159877 | 9789969 | 2.35342752 | 23.15 |
| 5 | 4452610 | 12232641 | 2.74729675 | 27.00 |

Figure 6:
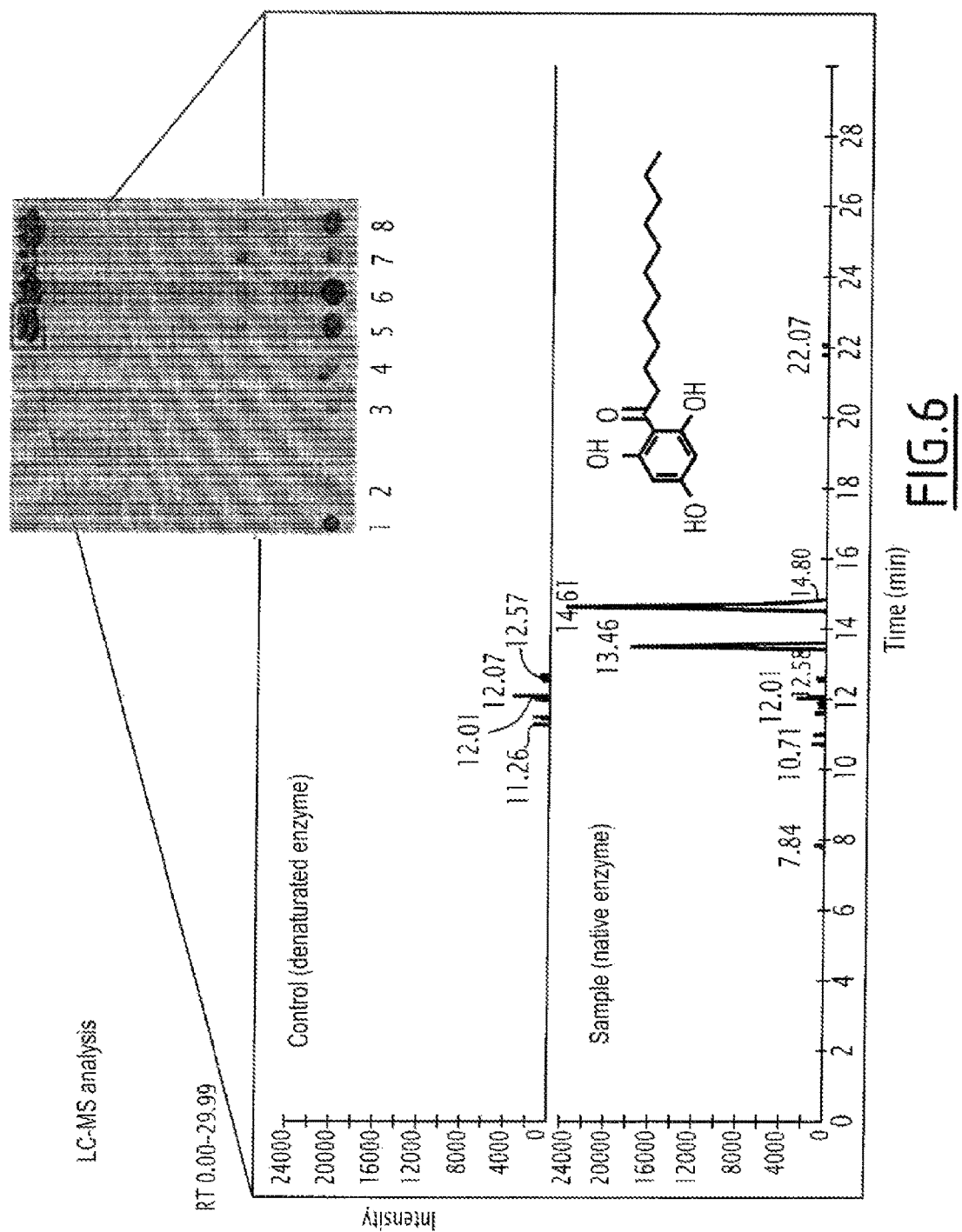
FIG. 6. represents the LC-MS mass spectrometry analysis of the products formed during the enzymatic reaction by using malonyl-CoA alone or malonyl-CoA+acetyl-CoA. 1: Negative control, 2: Denatured protein, 3: Malonyl-CoA, 4: Acetyl-CoA, 5: Lauroyl-CoA, 6: Palmitoyl-CoA, 7: Hexanoyl-CoA, 8: Decanoyl-CoA. NL parameters: $2.10^E4$, m/z: 307.1877-307.1939, MS b1.

LC-MS mass spectrometry analysis also allowed clear identification of the production of phloroglucinol from malonyl-CoA and acetyl-CoA (FIG. 6).

Figure 7:
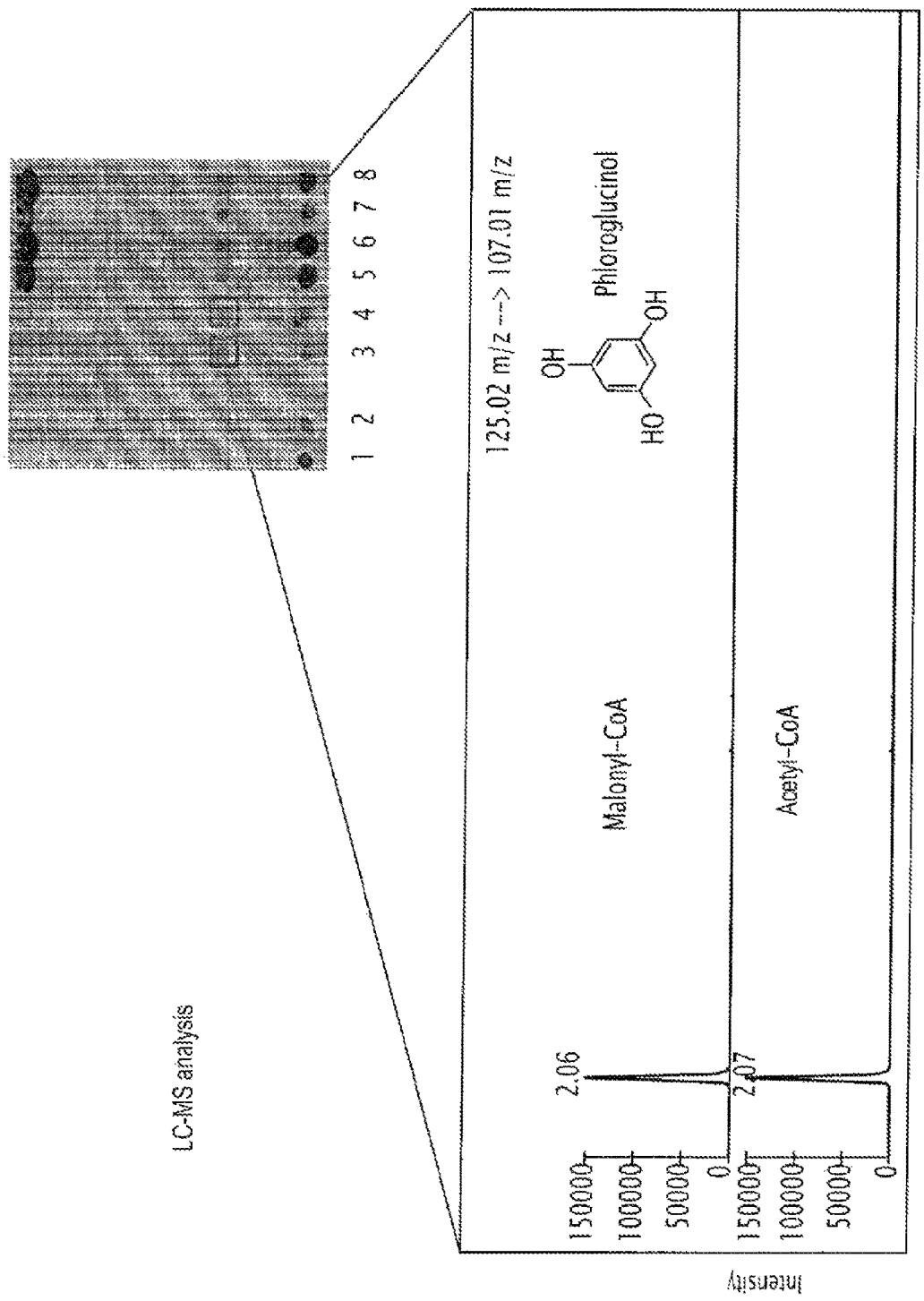
FIG. 7. represents the LC-MS mass spectrometry analysis of the products formed during the enzymatic reaction by using as a substrate malonyl-CoA and lauroyl-CoA. 1: Negative control, 2: Denatured protein, 3: Malonyl-CoA, 4: Acetyl-CoA, 5: Lauroyl-CoA, 6: Palmitoyl-CoA, 7: Hexanoyl-CoA, 8: Decanoyl-CoA.

The formation of the acyl-phloroglucinols was detected by specifically extracting the compounds present on TLC and by analyzing them with LC-MS mass spectrometry. Thus, for example, in the presence of malonyl-CoA and lauroyl-CoA, the enzyme PKS1 produces lauroyl-phloroglucinol (FIG. 7).

Other GC-MS analysis results for products formed in the presence of the different acyl-CoAs also suggest the formation of compounds of the tetraketide pyrone type like in *Mycobacterium tuberculosis*.

2.4. Crystallization and Obtaining the Structure of the PKS1 Enzyme

After obtaining crystallization conditions, several crystals of the PKS1 enzyme gave the possibility of obtaining sets of X-ray diffraction data allowing the resolution of the structure at 2.85 Å by the molecular replacement technique (Table 6).

TABLE 6

Collected data and purity statistics of PKS at a resolution of 2.85 Å.

| Collecting the data | High resolution PKS |
|---|---|
| Beamline ESRF | ID23-1 |
| Wavelength (Å) | 0.979239 |
| Space group | $P2_12_12_1$ |
| Lattice parameters Å) | A = 61.99, b = 83.92, c = 154.91 |
| Resolution (Å) | 83.920-2.85 (3.02-2.85) |
| Number of observations (F > 0) | 93096 (12976) |
| Number of single reflections | 22949 (3105) |
| Completion (%) | 100 (100) |
| Average I/(I) | 3.8 (1.4) |
| $R_{pim}$ (%) | 13.3 (58.7) |
| Redundancy | 4.1 (4.2) |
| Refinement | |
| Resolution | 56.917-2.85 |
| Number of single reflections | 21715 |
| R factor ($R_{free}$ on 5%) | 30.17 (41.31) |
| Number of atoms/protein (factor B average in Å$^2$) | 5768 (45.86) |
| Number of atoms of solvent (factor B average in Å$^2$) | 4 (34.20) |
| Standard deviation on the bonds (Å) | 0.013 |
| Standard deviation on the angles (°) | 1.736 |
| B factor average (Å$^2$) | 45.769 |

These data confirm the formation of a PKS1 dimer for the enzyme in its active recombinant form.

The overall structure of a PKS1 monomer reveals a composition with α helices and β sheaths organized in a canonical fold of the αβαβα-thiolase type. The catalytic triad is represented by the residues Cys194, His331 and Asn364. Like the PKSIII of *Mycobacterium tuberculosis*, designated as PKS18, PKS1 seems to have a tunnel for accessing the catalytic site where acyl-CoAs with more or less long chains may step in. The potential binding site of malonyl-CoA was also identified.

The invention claimed is:

1. A method for producing at least one polyphenol compound, comprising:

contacting a polyketide synthase of type III (PKSIII) from brown algae of the *Ectocarpus* genus with at least one carbonaceous substrate chosen from malonyl-CoA, acetyl-CoA, hexanoyl-CoA, decanoyl-CoA, lauroyl-CoA, and/or palmitoyl-CoA, under conditions allowing production of at least one polyphenol compound, wherein said polyphenol compound is phloroglucinol or an acyl-phloroglucinol, wherein said PKSIII comprises:

the amino acid sequence of SEQ ID NO: 1;

an amino acid sequence having at least 93% identity with the amino acid sequence of SEQ ID NO: 1;

and a tag sequence coding for a repetition of histidines before or after the coding sequence of said PKSIII.

2. The method according to claim 1, wherein said carbonaceous substrate is malonyl-CoA and said polyphenol compound is phloroglucinol.

3. The method according to claim 1, wherein said carbonaceous substrate is malonyl-CoA and lauroyl-CoA and said polyphenol compound is lauroyl-phloroglucinol.

* * * * *

UNITED STATES PATENT AND TRADEMARK OFFICE
CERTIFICATE OF CORRECTION

PATENT NO.        : 10,179,921 B2
APPLICATION NO.   : 14/348490
DATED             : January 15, 2019
INVENTOR(S)       : Ludovic Delage et al.

It is certified that error appears in the above-identified patent and that said Letters Patent is hereby corrected as shown below:

On the Title Page

(71) Applicants should read: UNIVERSITÉ PIERRE ET MARIE CURIE (PARIS 6), Paris (FR); UNIVERSITÉ DE BRETAGNE OCCIDENTALE, Brest (FR)

(73) Assignees should read: UNIVERSITÉ PIERRE ET MARIE CURIE (PARIS 6), Paris (FR); UNIVERSITÉ DE BRETAGNE OCCIDENTALE, Brest (FR)

Signed and Sealed this
Fourteenth Day of April, 2020

Andrei Iancu
*Director of the United States Patent and Trademark Office*

SEQUENCE LISTING

<160> NUMBER OF SEQ ID NOS: 12

<210> SEQ ID NO 1
<211> LENGTH: 290
<212> TYPE: PRT
<213> ORGANISM: Ectocarpus siliculosus

<400> SEQUENCE: 1

```
Val Leu Glu Arg Ile Tyr Gly Asn Ser Arg Ile Gly Ser Arg Tyr Phe
 1               5                  10                  15

Ala Val Pro Asp Phe Thr Pro Gly Arg Ala Ala Lys Gly Asp Pro Leu
            20                  25                  30

Phe Tyr Pro Ala Asp Gly Ser Tyr Gln Val Pro Val Asp Val Arg Leu
        35                  40                  45

Asp Lys Phe Lys Glu Lys Ala Val Pro Leu Val Ser Asp Val Ala Arg
    50                  55                  60

Arg Ala Ile Lys Glu Ala Gly Leu Asn Val Glu Asp Ile Ser Lys Leu
65                  70                  75                  80

Val Val Val Ser Ser Thr Gly Phe Leu Gly Pro Gly Leu Asp Cys Glu
                85                  90                  95

Leu Ile Lys Asn Leu Gly Leu Thr Arg Ser Val Asp Arg Thr Leu Ile
            100                 105                 110

Gly Phe Met Gly Cys Ala Ala Ala Met Asn Gly Phe Arg Asn Ala Asn
        115                 120                 125

Asp Tyr Val Thr Ala Asn Pro Gly Lys Tyr Ala Leu Met Ile Cys Val
    130                 135                 140

Glu Leu Ser Ser Val His Thr Thr Phe Asp Asp Asn Ile Asn Asp Ala
145                 150                 155                 160

Ile Leu His Ala Ile Phe Ala Asp Gly Cys Ala Ala Ala Val Leu Lys
                165                 170                 175

Gly Ala Arg Lys Ser Glu Cys Pro Lys Gly Thr Leu Ala Ile Val Asp
            180                 185                 190

Asn His Ala Trp Leu Met Glu Gly Thr Glu Asp Gly Ile Thr Leu Ala
        195                 200                 205

Ile Lys Pro Asn Gly Ile Thr Cys Thr Leu Ser Lys Phe Leu Pro Gln
    210                 215                 220

Tyr Ile Ala Lys Asn Ile Ala Phe Phe Ala Asp Gly Phe Leu Lys Lys
225                 230                 235                 240

His Lys Leu Gly Arg Asp Asp Val Asp Phe Trp Cys Val His Pro Gly
                245                 250                 255

Gly Arg Arg Ile Ile Glu Glu Ala Gln Asn Gly Leu Gly Leu Ser Glu
            260                 265                 270

Glu Gln Thr Ala Asp Ser Trp Ala Val Leu Gly Glu Tyr Gly Asn Met
        275                 280                 285

Leu Ser
    290
```

<210> SEQ ID NO 2
<211> LENGTH: 870
<212> TYPE: DNA
<213> ORGANISM: Ectocarpus siliculosus

<400> SEQUENCE: 2

```
gttctcgagc gcatctacgg caactcgcgc atcggcagcc gctacttcgc cgtgccggac      60 ttcaccccg gcagggcggc caagggcgac cccctcttct acccggccga cggcagctac     120
```

```
caggtgcccg tggacgtccg gctggacaag ttcaaggaga aggccgtccc gctggtgtcc    180
gacgtcgccc gccgcgccat caaggaggcc ggcctgaacg tcgaggacat ctccaagctc    240
gtcgtggtct cctccaccgg attcctcggc cccggcctcg actgcgagct gatcaagaac    300
ctcggcctga cccgctccgt cgaccgcacc ctcatcgggt tcatgggctg cgccgccgcc    360
atgaacggtt tccgtaacgc gaacgactac gtcaccgcca accccggaaa gtacgcgctg    420
atgatctgcg tcgagctttc ctcggtgcac acgaccttg acgacaacat caacgacgcg    480
atcttgcacg ctatcttcgc cgacggatgc gccgctgccg tgctcaaggg agccaggaag    540
tcggagtgcc ccaagggaac cctcgctatc gtcgacaacc acgcgtggct catggaggga    600
accgaggacg gaatcaccct tgctatcaag ccaaacggca tcacctgcac cctgtccaag    660
ttcctgcccc agtacatcgc caagaacatc gccttcttcg cggacggctt cctcaagaag    720
cacaagctcg gacgcgacga cgttgacttc tggtgcgtgc accccggagg ccgacgtatc    780
atcgaggagg cgcagaacgg ccttggcctc tcggaggagc agaccgcgga ctcgtgggcg    840
gtgctcgggg agtacggaaa catgctctcg                                    870
```

<210> SEQ ID NO 3
<211> LENGTH: 380
<212> TYPE: PRT
<213> ORGANISM: Ectocarpus siliculosus

<400> SEQUENCE: 3

```
Ser Lys Asp Glu Gln Thr Val Tyr Pro Val Ile Ala Gly Met Ala Ile
1               5                   10                  15

Gly Asn Pro Gln Tyr Arg Cys Thr Gln Asn Glu Ala Leu Ala Val Ala
                20                  25                  30

Ser Lys Cys Pro Gly Leu Glu Ser Ile Lys Pro Val Leu Glu Arg Ile
            35                  40                  45

Tyr Gly Asn Ser Arg Ile Gly Ser Arg Tyr Phe Ala Val Pro Asp Phe
        50                  55                  60

Thr Pro Gly Arg Ala Ala Lys Gly Asp Pro Leu Phe Tyr Pro Ala Asp
65                  70                  75                  80

Gly Ser Tyr Gln Val Pro Val Asp Val Arg Leu Asp Lys Phe Lys Glu
                85                  90                  95

Lys Ala Val Pro Leu Val Ser Asp Val Ala Arg Arg Ala Ile Lys Glu
            100                 105                 110

Ala Gly Leu Asn Val Glu Asp Ile Ser Lys Leu Val Val Ser Ser
        115                 120                 125

Thr Gly Phe Leu Gly Pro Gly Leu Asp Cys Glu Leu Ile Lys Asn Leu
130                 135                 140

Gly Leu Thr Arg Ser Val Asp Arg Thr Leu Ile Gly Phe Met Gly Cys
145                 150                 155                 160

Ala Ala Ala Met Asn Gly Phe Arg Asn Ala Asn Asp Tyr Val Thr Ala
                165                 170                 175

Asn Pro Gly Lys Tyr Ala Leu Met Ile Cys Val Glu Leu Ser Ser Val
            180                 185                 190

His Thr Thr Phe Asp Asp Asn Ile Asn Asp Ala Ile Leu His Ala Ile
        195                 200                 205

Phe Ala Asp Gly Cys Ala Ala Ala Val Leu Lys Gly Ala Arg Lys Ser
    210                 215                 220

Glu Cys Pro Lys Gly Thr Leu Ala Ile Val Asp Asn His Ala Trp Leu
225                 230                 235                 240
```

```
Met Glu Gly Thr Glu Asp Gly Ile Thr Leu Ala Ile Lys Pro Asn Gly
                245                 250                 255

Ile Thr Cys Thr Leu Ser Lys Phe Leu Pro Gln Tyr Ile Ala Lys Asn
            260                 265                 270

Ile Ala Phe Phe Ala Asp Gly Phe Leu Lys Lys His Lys Leu Gly Arg
        275                 280                 285

Asp Asp Val Asp Phe Trp Cys Val His Pro Gly Gly Arg Arg Ile Ile
    290                 295                 300

Glu Glu Ala Gln Asn Gly Leu Gly Leu Ser Glu Gln Thr Ala Asp
305                 310                 315                 320

Ser Trp Ala Val Leu Gly Glu Tyr Gly Asn Met Leu Ser Pro Ser Val
                325                 330                 335

Met Phe Val Leu Ser Arg Val Phe Lys Arg His Asn Ala Ala Leu Ala
            340                 345                 350

Gln Gly Lys Pro Gly Tyr Gln Thr Gly Met Ala Phe Ser Phe Ser Pro
        355                 360                 365

Gly Val Gly Ala Glu Gly Ile Leu Leu Arg Gln Ile
    370                 375                 380

<210> SEQ ID NO 4
<211> LENGTH: 1143
<212> TYPE: DNA
<213> ORGANISM: Ectocarpus siliculosus

<400> SEQUENCE: 4
tccaaggacg agcagacggt atacccggtc atcgccggga tggccatcgg caacccgcag      60
taccgctgca cgcagaacga ggccctcgcc gtcgcctcca agtgcccggg cctcgagtcc     120
atcaagcccg ttctcgagcg catctacggc aactcgcgca tcggcagccg ctacttcgcc     180
gtgccggact caccccccgg cagggcggcc aagggcgacc ccctcttcta cccggccgac     240
ggcagctacc aggtgcccgt ggacgtccgg ctggacaagt tcaaggagaa ggccgtcccg     300
ctggtgtccg acgtcgcccg ccgcgccatc aaggaggccg gcctgaacgt cgaggacatc     360
tccaagctcg tcgtggtctc ctccaccgga ttcctcggcc ccggcctcga ctgcgagctg     420
atcaagaacc tcggcctgac ccgctccgtc gaccgcaccc tcatcgggtt catgggctgc     480
gccgccgcca tgaacggttt ccgtaacgcg aacgactacg tcaccgccaa ccccggaaag     540
tacgcgctga tgatctgcgt cgagctttcc tcggtgcaca cgacctttga cgacaacatc     600
aacgacgcga tcttgcacgc tatcttcgcc gacggatgcg ccgctgccgt gctcaaggga     660
gccaggaagt cggagtgccc caagggaacc ctcgctatcg tcgacaacca cgcgtggctc     720
atggagggaa ccgaggacgg aatcacccct gctatcaagc caaacggcat cacctgcacc     780
ctgtccaagt tcctgcccca gtacatcgcc aagaacatcg ccttcttcgc ggacggcttc     840
ctcaagaagc acaagctcgg acgcgacgac gttgacttct ggtgcgtgca ccccggaggc     900
cgacgtatca tcgaggaggc gcagaacggc cttggcctct cggaggagca gaccgcggac     960
tcgtgggcgg tgctcgggga gtacggaaac atgctctcgc cctccgttat gttcgttctg    1020
tctagggttt tcaagcgcca caacgccgcg ctcgcacagg gcaagcccgg ctaccagacg    1080
ggtatggcgt tctccttctc gccgggtgtc ggggcagagg gcatccttct caggcagatc    1140
tag                                                                   1143

<210> SEQ ID NO 5
<211> LENGTH: 102
<212> TYPE: DNA
```

<213> ORGANISM: Ectocarpus siliculosus

<400> SEQUENCE: 5

```
atgtcttctg ctgcggttgc tatgctggct gacccgactg tccagatcgc tctggcgtgc      60
ctggtggtgt ctctcttcgt tgtgctgcag tcggtcaaaa ag                        102
```

<210> SEQ ID NO 6
<211> LENGTH: 34
<212> TYPE: PRT
<213> ORGANISM: Ectocarpus siliculosus

<400> SEQUENCE: 6

```
Met Ser Ser Ala Ala Val Ala Met Leu Ala Asp Pro Thr Val Gln Ile
1               5                   10                  15

Ala Leu Ala Cys Leu Val Val Ser Leu Phe Val Val Leu Gln Ser Val
            20                  25                  30

Lys Lys
```

<210> SEQ ID NO 7
<211> LENGTH: 6
<212> TYPE: PRT
<213> ORGANISM: Artificial Sequence
<220> FEATURE:
<223> OTHER INFORMATION: Sequence etiquette

<400> SEQUENCE: 7

```
His His His His His His
1               5
```

<210> SEQ ID NO 8
<211> LENGTH: 18
<212> TYPE: DNA
<213> ORGANISM: Artificial Sequence
<220> FEATURE:
<223> OTHER INFORMATION: Sequence etiquette
<220> FEATURE:
<221> NAME/KEY: misc_feature
<222> LOCATION: (3)..(3)
<223> OTHER INFORMATION: y = c ou t
<220> FEATURE:
<221> NAME/KEY: misc_feature
<222> LOCATION: (6)..(6)
<223> OTHER INFORMATION: y = c ou t
<220> FEATURE:
<221> NAME/KEY: misc_feature
<222> LOCATION: (9)..(9)
<223> OTHER INFORMATION: y = c ou t
<220> FEATURE:
<221> NAME/KEY: misc_feature
<222> LOCATION: (12)..(12)
<223> OTHER INFORMATION: y = c ou t
<220> FEATURE:
<221> NAME/KEY: misc_feature
<222> LOCATION: (15)..(15)
<223> OTHER INFORMATION: y = c ou t
<220> FEATURE:
<221> NAME/KEY: misc_feature
<222> LOCATION: (18)..(18)
<223> OTHER INFORMATION: y = c ou t

<400> SEQUENCE: 8

```
caycaycayc aycaycay                                                   18
```

<210> SEQ ID NO 9
<211> LENGTH: 12
<212> TYPE: PRT
<213> ORGANISM: Artificial Sequence
<220> FEATURE:

```
<223> OTHER INFORMATION: Sequence etiquette

<400> SEQUENCE: 9

Met Arg Gly Ser His His His His His His Gly Ser
1               5                   10

<210> SEQ ID NO 10
<211> LENGTH: 36
<212> TYPE: DNA
<213> ORGANISM: Artificial Sequence
<220> FEATURE:
<223> OTHER INFORMATION: Sequence etiquette

<400> SEQUENCE: 10
atgcgcggca gccatcatca tcatcatcat ggcagc                         36

<210> SEQ ID NO 11
<211> LENGTH: 54
<212> TYPE: DNA
<213> ORGANISM: Artificial Sequence
<220> FEATURE:
<223> OTHER INFORMATION: Amorce de clonage

<400> SEQUENCE: 11
ggcggatccg catgcatgtc caaggacgag cagacggtat acccggtcat cgcc     54

<210> SEQ ID NO 12
<211> LENGTH: 46
<212> TYPE: DNA
<213> ORGANISM: Artificial Sequence
<220> FEATURE:
<223> OTHER INFORMATION: Amorce de clonage

<400> SEQUENCE: 12
ggctaagctt ttactagatc tgcctgagaa ggatgccctc tgcccc              46
```